(12) United States Patent
Yu

(10) Patent No.: US 8,146,874 B2
(45) Date of Patent: Apr. 3, 2012

(54) MOUNTING SUPPORT ASSEMBLY FOR SUSPENDING A MEDICAL INSTRUMENT DRIVER ABOVE AN OPERATING TABLE

(75) Inventor: Alan L. Yu, Union City, CA (US)

(73) Assignee: Hansen Medical, Inc., Mountain View, CA (US)

( * ) Notice: Subject to any disclaimer, the term of this patent is extended or adjusted under 35 U.S.C. 154(b) by 852 days.

(21) Appl. No.: 12/024,883

(22) Filed: Feb. 1, 2008

(65) Prior Publication Data

US 2008/0245946 A1    Oct. 9, 2008

Related U.S. Application Data

(60) Provisional application No. 60/899,048, filed on Feb. 2, 2007, provisional application No. 60/900,584, filed on Feb. 8, 2007.

(51) Int. Cl.
*A47G 1/10* (2006.01)
(52) U.S. Cl. ............. 248/316.1; 248/316.4; 248/346.07; 108/98; 297/251; 5/507.1
(58) Field of Classification Search ............. 248/229.16, 248/229.11, 447, 2, 411, 316.5, 231.51, 124, 248/229.14, 227.1, 227.2, 228.3, 346.07, 248/231.61, 229.24, 361.1, 245, 250, 316.4; 108/98, 97, 137, 158.13; 297/251, 252, 250.1; 5/507.1
See application file for complete search history.

(56) References Cited

U.S. PATENT DOCUMENTS 1,598,569 A * 8/1926 Fitzhugh .......................... 108/49
(Continued)

FOREIGN PATENT DOCUMENTS
EP    1290982    3/2003
(Continued)

OTHER PUBLICATIONS

PCT International Search Report and Written Opinion of the International Search Authority for PCT/US2008/052814, Applicant Hansen Medical, Inc., Forms PCT/ISA/210, 220 and 237, dated Sep. 2, 2008 (11 pages).

*Primary Examiner* — Kimberly Wood
(74) *Attorney, Agent, or Firm* — Vista IP Law Group LLP

(57) ABSTRACT

An adapter plate assembly which provides a convenient interface between a mounting support assembly for suspending an instrument driver robotic instrument system above a operating table. The adapter plate securely mounts to the operating table, and may be adjustable so that it can be adjusted to fit various sizes and models of operating tables. The adapter plate assembly comprises a main plate which rests on the surface of the operating table. A first clamp assembly which removably attaches to the operating table is mounted on one or more horizontal adjustment rods which are slidably received in one of the main plate in order to provide adjustability to the width of the adapter plate assembly. On the opposing end of the main plate, a second clamp assembly is coupled main plate. In order to secure the support assembly of a robotic instrument system, an adapter rail is also coupled to the main plate. The adapter rail is configured to detachably couple to a support assembly interface of the support assembly, and provides sufficient structural support for suspending the instrument driver above the operating table.

13 Claims, 19 Drawing Sheets

U.S. PATENT DOCUMENTS

| | | | | |
|---|---|---|---|---|
| 2,048,449 A | * | 7/1936 | Holtzmann | 248/231.41 |
| 2,466,518 A | * | 4/1949 | Wagner | 269/91 |
| 2,569,729 A | * | 10/1951 | Nold | 297/250.1 |
| 2,940,715 A | * | 6/1960 | Schultz et al. | 248/231.41 |
| 2,970,798 A | * | 2/1961 | Friotchle et al. | 248/229.25 |
| 3,495,519 A | * | 2/1970 | Bluitt et al. | 108/137 |
| 4,432,525 A | * | 2/1984 | Duvall | 248/430 |
| 4,729,336 A | * | 3/1988 | Rohne | 114/363 |
| 4,766,838 A | * | 8/1988 | Johnson | 114/363 |
| 4,773,709 A | * | 9/1988 | Slinkard | 297/188.09 |
| 5,112,015 A | * | 5/1992 | Williams | 248/236 |
| 5,330,147 A | * | 7/1994 | Volcheff et al. | 248/316.4 |
| 5,590,619 A | * | 1/1997 | Meador et al. | 114/363 |
| 5,960,746 A | * | 10/1999 | Salts | 119/756 |
| 6,070,584 A | | 6/2000 | Bergström | |
| 6,189,478 B1 | * | 2/2001 | Myers et al. | 114/344 |
| 2002/0161446 A1 | | 10/2002 | Bryan et al. | |
| 2005/0045785 A1 | * | 3/2005 | Cohen | 248/214 |
| 2005/0137478 A1 | | 6/2005 | Younge et al. | |
| 2005/0197530 A1 | | 9/2005 | Wallace et al. | |
| 2005/0222554 A1 | | 10/2005 | Wallace et al. | |
| 2006/0084945 A1 | | 4/2006 | Moll et al. | |
| 2006/0095022 A1 | | 5/2006 | Moll et al. | |
| 2006/0111692 A1 | | 5/2006 | Hlavka et al. | |
| 2006/0200026 A1 | | 9/2006 | Wallace et al. | |
| 2006/0253108 A1 | | 11/2006 | Yu et al. | |
| 2006/0276775 A1 | | 12/2006 | Rosenberg et al. | |
| 2007/0043338 A1 | | 2/2007 | Moll et al. | |
| 2007/0094798 A1 | | 5/2007 | Yu | |
| 2007/0156123 A1 | | 7/2007 | Moll et al. | |
| 2007/0197896 A1 | | 8/2007 | Moll et al. | |

FOREIGN PATENT DOCUMENTS

TW  M296033  8/2006

* cited by examiner

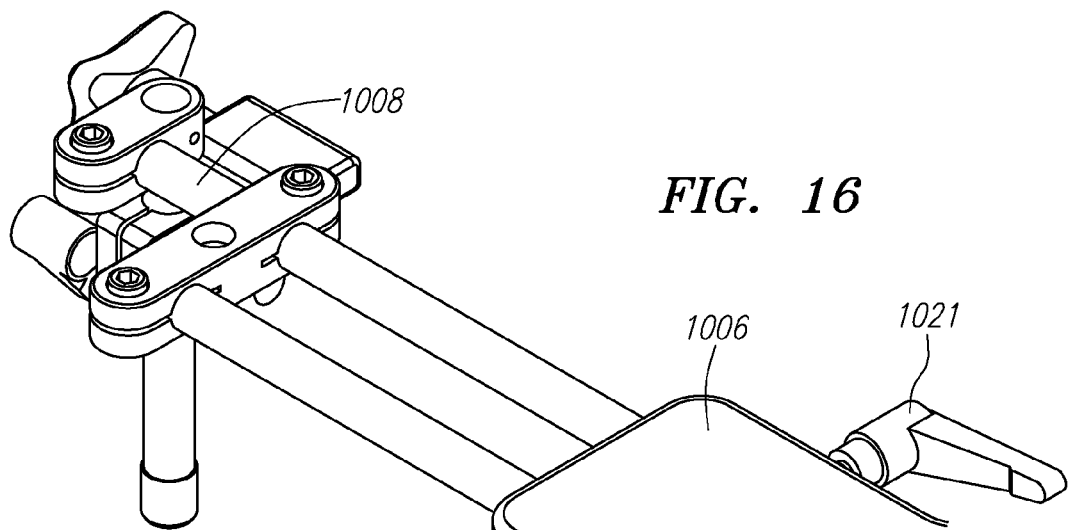
FIG. 16
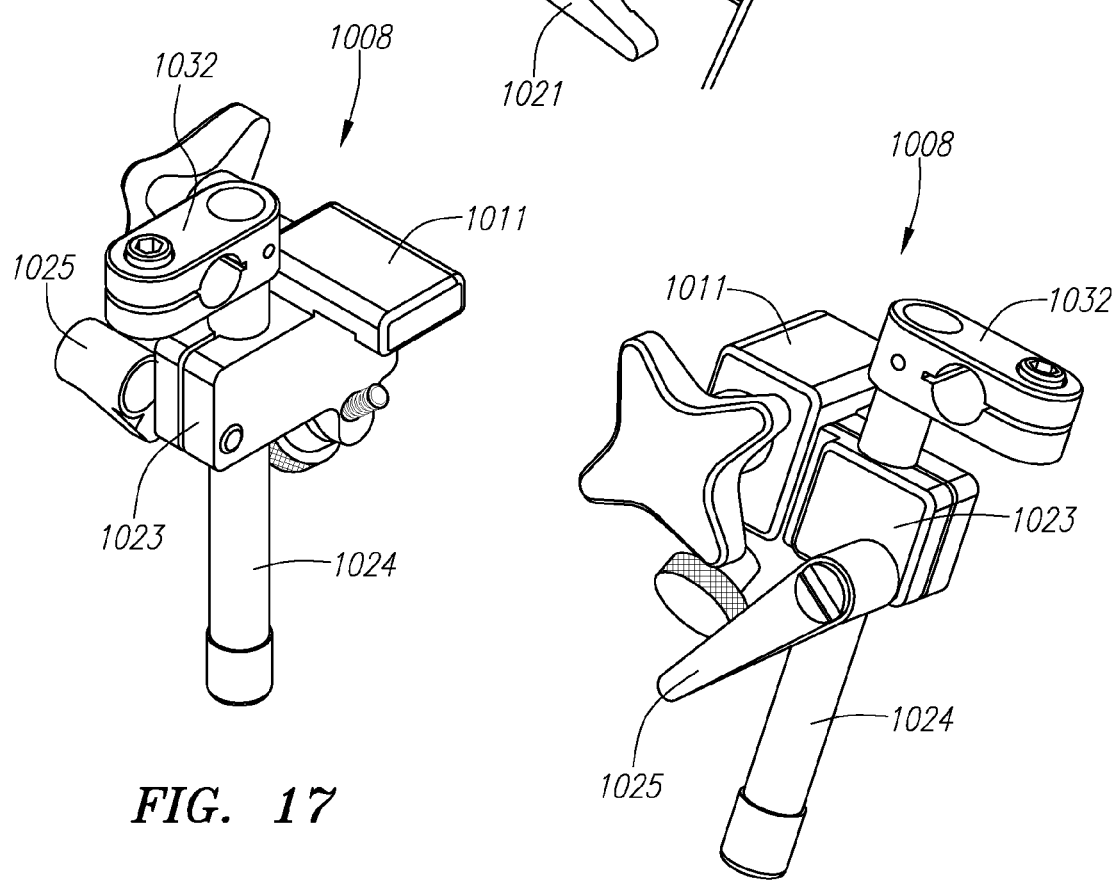
FIG. 17
FIG. 18

MOUNTING SUPPORT ASSEMBLY FOR SUSPENDING A MEDICAL INSTRUMENT DRIVER ABOVE AN OPERATING TABLE

RELATED APPLICATION DATA

The present application claims the benefit under 35 U.S.C. §119 to U.S. Provisional Patent Application Ser. Nos. 60/899,048, filed on Feb. 2, 2007, and 60/900,584, filed on Feb. 8, 2007. The foregoing applications are hereby incorporated by reference into the present application in its entirety.

FIELD OF INVENTION

The invention relates generally to robotically controlled medical instrument systems, such as telerobotic surgical systems, and more particularly to a mounting support assembly for suspending a robotically controlled instrument driver over an operating table for performing minimally invasive diagnostic and therapeutic medical procedures.

BACKGROUND

Robotic interventional systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels, other lumens, via surgically-created wounds of minimized size, or combinations thereof.

SUMMARY OF THE INVENTION

The present invention is directed to an adapter plate assembly which provides a convenient interface between a mounting support assembly for suspending an instrument driver of robotic instrument system above a operating table. The adapter plate securely mounts to the operating table, and may be adjustable so that it can be adjusted to fit various sizes and models of operating tables. Then, a component of the robotic instrument system, such as a support assembly having a plurality of adjustable arms for supporting an instrument, may be secured to the adapter plate assembly.

In one embodiment, the adapter plate assembly comprises a substantially flat main plate comprising a top surface, a bottom surface, first and second ends and first and second sides. The main plate rests on the surface of the operating table. A first clamp assembly is coupled to the main plate and has a clamp configured for removable attachment to the operating table. For example, the clamp may be configured with an L-shaped body that mates to a table rail of a operating table and has one or more set screws to lock the clamp to the rail. In order to provide adjustability to the width of the adapter plate assembly, the first clamp assembly may be mounted on one or more horizontal adjustment rods which are slidably received in the first end of the main plate. The horizontal adjustment rods can simply be extended and retracted from the main plate so as to adjust the width of the adapter plate assembly to accommodate the width of the operating table. A first locking device is also provided on the main plate for securing the horizontal adjustment rods in a desired position.

On the opposing end of the main plate, a second clamp assembly is coupled to the second end of the main plate. A third clamp assembly may also be provided on the second end of the main plate, in which case the second and third clamps can be placed near the first and second sides of the main plate, respectively. The second and third clamps may be the same or similar to the first clamp described above.

In order to secure the support assembly of a robotic instrument system, an adapter rail is coupled to the second end of the main plate. The adapter rail is configured to detachably couple to a support assembly interface of the support assembly, and provides sufficient structural support for the robotic instrument system.

In order to provide vertical adjustment of the adapter plate assembly, each clamp may comprise a locking device which couples to a respective vertical adjustment rod. In turn, the vertical adjustment rods are coupled to the main plate. In this way, the clamps can be adjusted vertically on their respective vertical adjustment rods, and then the locking devices can be locked to secure the clamps at the desired vertical location. As a safety mechanism, the locking devices may comprises ratcheting knobs that must pushed inward in order to rotate the locking device thereby releasing or locking the locking device, as the case may be.

BRIEF DESCRIPTION OF THE DRAWINGS

The drawings illustrate the design and utility of illustrated embodiments of the invention, in which similar elements are referred to by common reference numerals.

FIGS. 9A-10 illustrate one embodiment of a clamp assembly;

FIG. 16 illustrates an enlarged view of the portion of one embodiment of an adapter plate assembly near the surgeon side;

FIGS. 17-18 illustrate one embodiment of clamp assemblies;

DETAILED DESCRIPTION OF THE ILLUSTRATED EMBODIMENTS

The present invention is directed to various embodiments of mounting platforms for mounting an instrument driver of a robotic instrument system to an operating table. The mounting platform, along with the mounted support assembly can be used to support and adjust the position of the instrument driver on or near an operating table. It is to be understood that each of the embodiments described herein may be utilized with robotic instrument systems, which can control the positioning of the devices within a patients body, and may also control the operation of other functions of the devices, such as imaging devices, ablation devices, cutting tools, or other end effectors, including without limitation all of the robotic instrument systems incorporated by reference below.

Figure 1A:
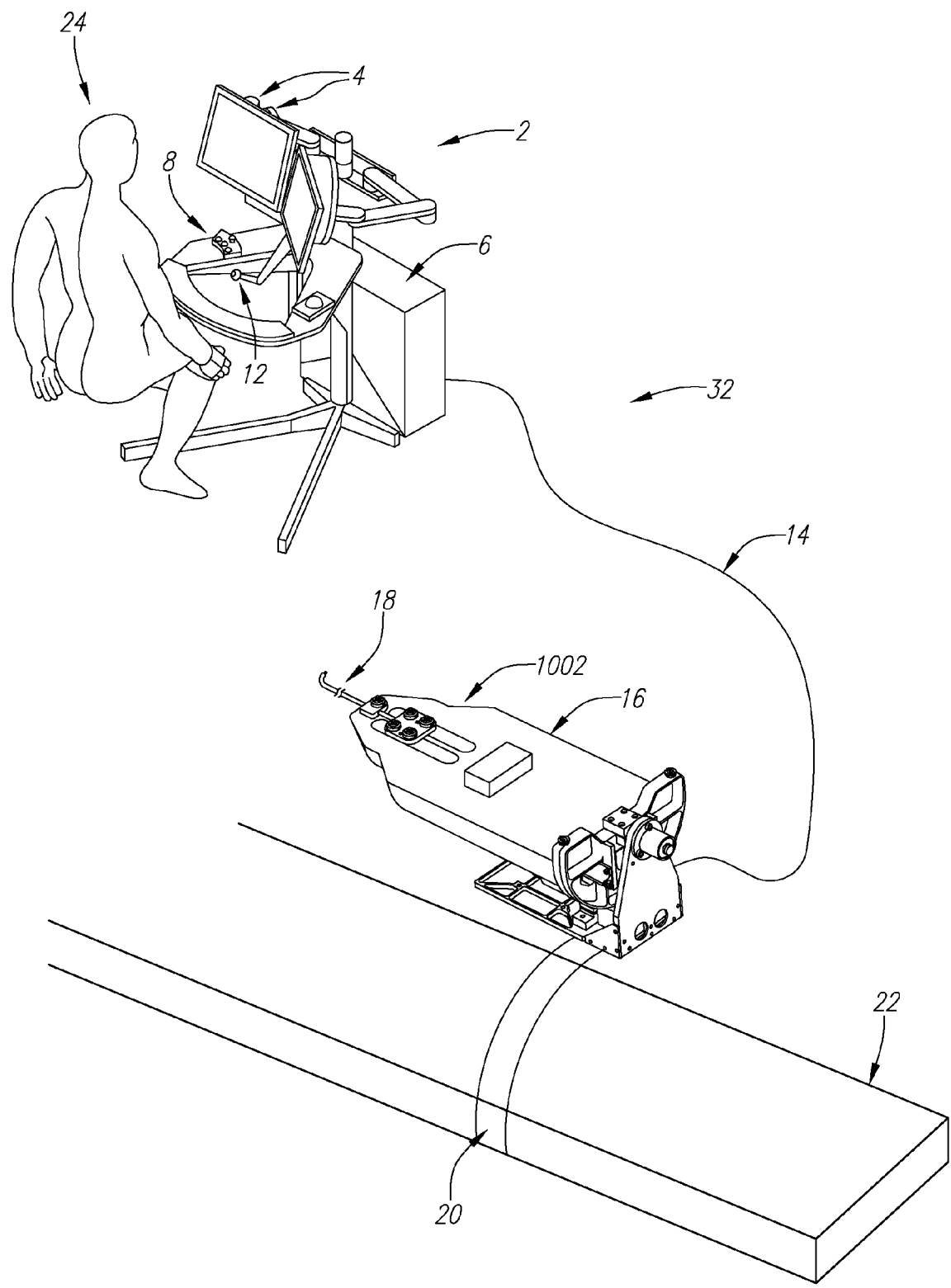
FIG. 1A illustrates a one embodiment of a robotic instrument system.

Referring to FIG. 1A, one embodiment of a robotic instrument system (32), includes an operator control station (2) located remotely from an operating table (22), and a robotic instrument assembly (1002). The robotic instrument assembly (1002) comprises an instrument driver (16) and an instrument (18) coupled to the operating table (22) by an instrument driver mounting brace (20). A communication link (14) transfers signals between the operator control station (2) and instrument driver (16). The instrument driver mounting brace (20) of the depicted embodiment is a relatively simple, arcuate-shaped structural member configured to position the instrument driver (16) above a patient (not shown) lying on the table (22).

Figure 1B:
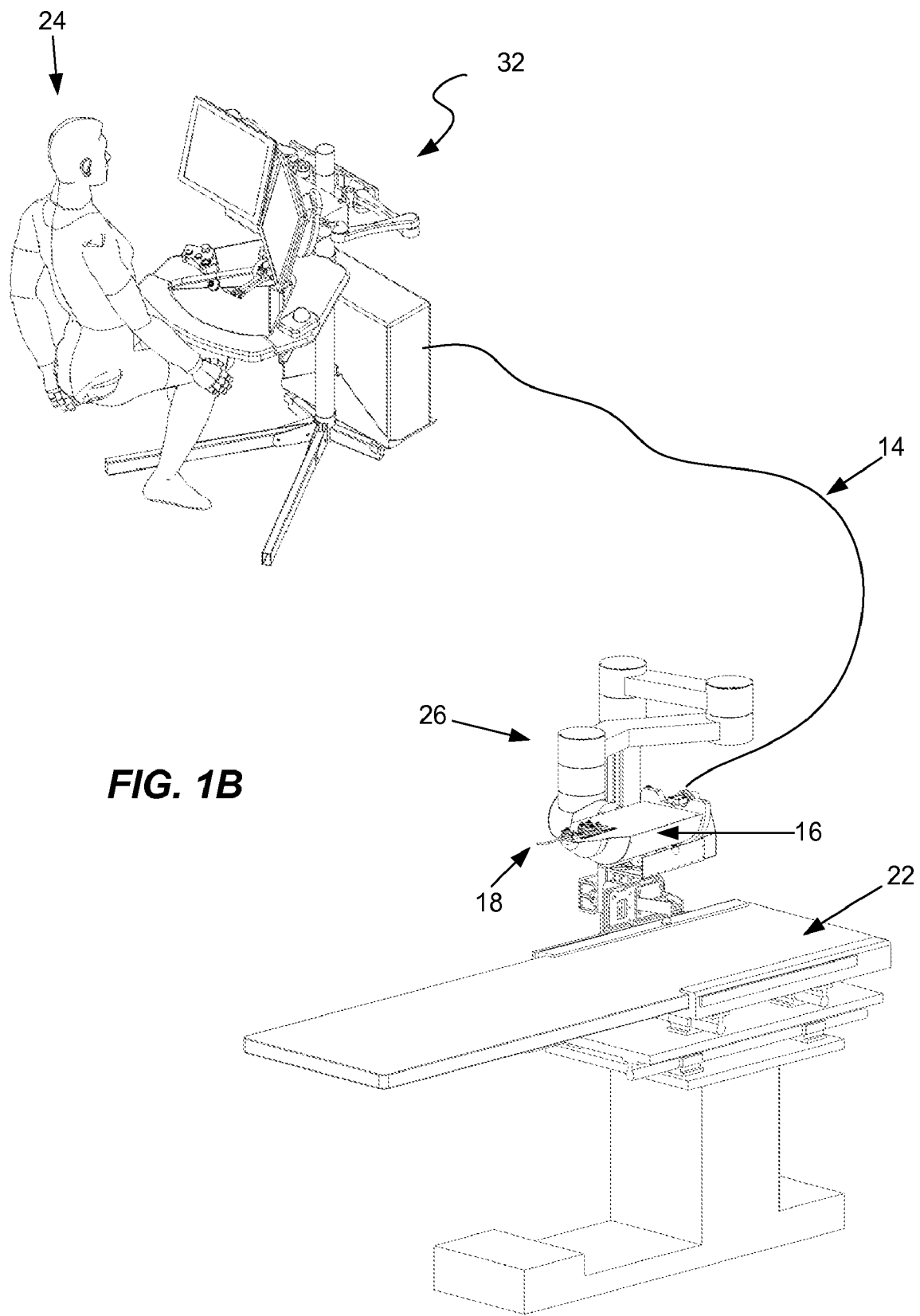
FIG. 1B illustrates another embodiment of a robotic instrument system.

In FIG. 1B, another embodiment of a robotic instrument system (32) is depicted, wherein the arcuate-shaped member (20) is replaced by a movable support assembly (26). The support assembly (26) is configured to movably support the instrument driver (16) above the operating table (22) in order to position the instrument driver (16) for convenient access into desired locations relative to a patient (not shown). The support assembly (26) in FIG. 1B is also configured to lock the instrument driver (16) into position once it is positioned.

The instrument (18) is typically an elongate, flexible device configured to be inserted into a patient's body. As non-limiting examples, an instrument (18) may comprise an intravascular catheter, an endoscopic surgical instrument or other medical instrument. The instrument (18) may also comprise an instrument assembly (28) comprising a robotic guide instrument (18), or a coaxially coupled and independently controllable robotic sheath instrument and a robotic guide instrument (18), as described in the U.S. patent applications incorporated by reference below. The instrument (18) or instrument assembly (28) is configured to be operable via the instrument driver (16) such that the instrument driver (16) can operate to steer the instrument (18) or instrument assembly (28) and also to operate tools and devices which may be provided on the instrument assembly (18) or instrument assembly (28) (e.g. an imaging device or cutting tool disposed on the distal end of the instrument (18) or instrument assembly (28)). Alternatively, manually steerable and operable instruments or instrument assemblies may also be utilized. Thus, the procedures described herein may be utilized with manually or robotically steerable instrument systems, such as those described in the below-referenced U.S. patent application Ser. No. 11/481,433.

Exemplary embodiments of an operator control station (2), an instrument driver (16), an instrument (18) or instrument assembly (28), a robotic sheath instrument, a robotic guide instrument (18), various instruments (50), are described in detail in the following U.S. patent applications, and are incorporated herein by reference in their entirety:

U.S. patent application Ser. Nos. 10/923,660, filed Aug. 20, 2004; 10/949,032, filed Sep. 24, 2005; 11/073,363, filed Mar. 4, 2005; 11/173,812, filed Jul. 1, 2005; 11/176,954, filed Jul. 6, 2005; 11/179,007, filed Jul. 6, 2005; 11/202,925, filed Aug. 12, 2005; 11/331,576, filed Jan. 13, 2006; 60/785,001, filed Mar. 22, 2006; 60/788,176, filed Mar. 31, 2006; 11/418,398, filed May 3, 2006; 11/481,433, filed Jul. 3, 2006; 11/637,951, filed Dec. 11, 2006; 11/640,099, filed Dec. 14, 2006; 60/833,624, filed Jul. 26, 2006, and 60/835,592, filed Aug. 3, 2006.

Figure 1C:
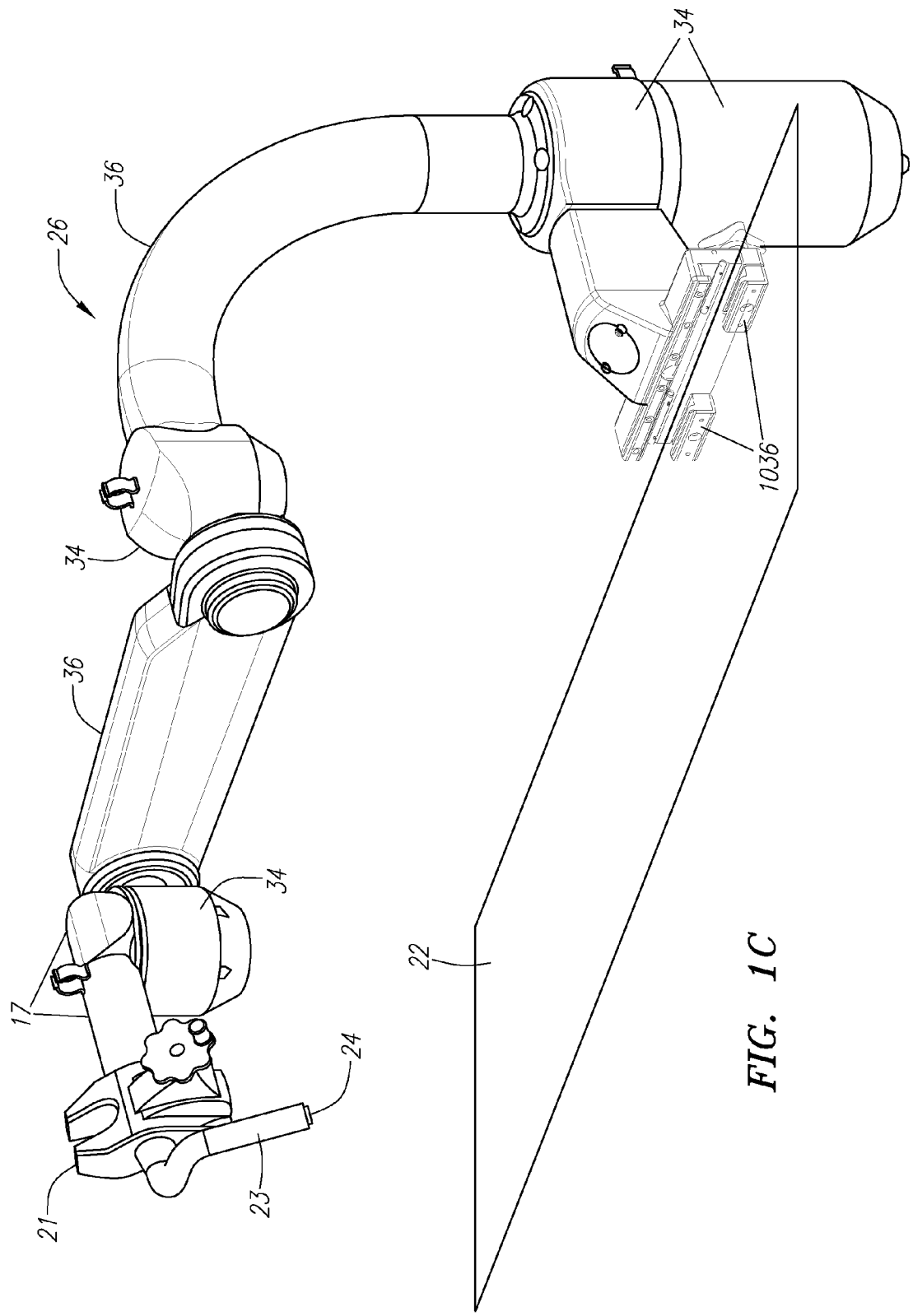
FIG. 1C illustrates one embodiment of a support assembly for supporting an instrument driver.

FIG. 1C provides a closer view of the support assembly (also referred to as a setup joint) (26) depicted in the embodiment of FIG. 1B. The support assembly (26) comprises a series of rigid links (36) coupled by electronically braked joints (34). The joints (34) allow motion of the links (36) when energized by a control system (not shown), but otherwise prevent motion of the links. The control system may be activated by a switch (e.g., a footswitch or thumbswitch), or computer interface. In another embodiment, the rigid links (36) may be coupled by mechanically lockable joints, which may be locked and unlocked manually using, for example, locking pins, screws, or clamps. The rigid links (36) preferably comprise a light but strong material, such as high-gage aluminum, shaped to withstand the stresses and strains associated with precisely maintaining a three-dimensional position of the approximately ten pound weight of a typical embodiment of the instrument driver (16) once the position of the link (36) is fixed. An instrument driver support shaft (17) is provided near the distal end of the support assembly (26), and is coupled to a pivotable instrument driver mounting interface (21) for attaching the instrument driver (16). The support assembly (26) also has an interface surface (1036) which may comprise one or more mounting clamps each generally comprising a fixed upper body portion having a mating surface, and upper and lower clamp toe portions configured for detachably coupling to a rail of an operating table (22).

Figure 2:
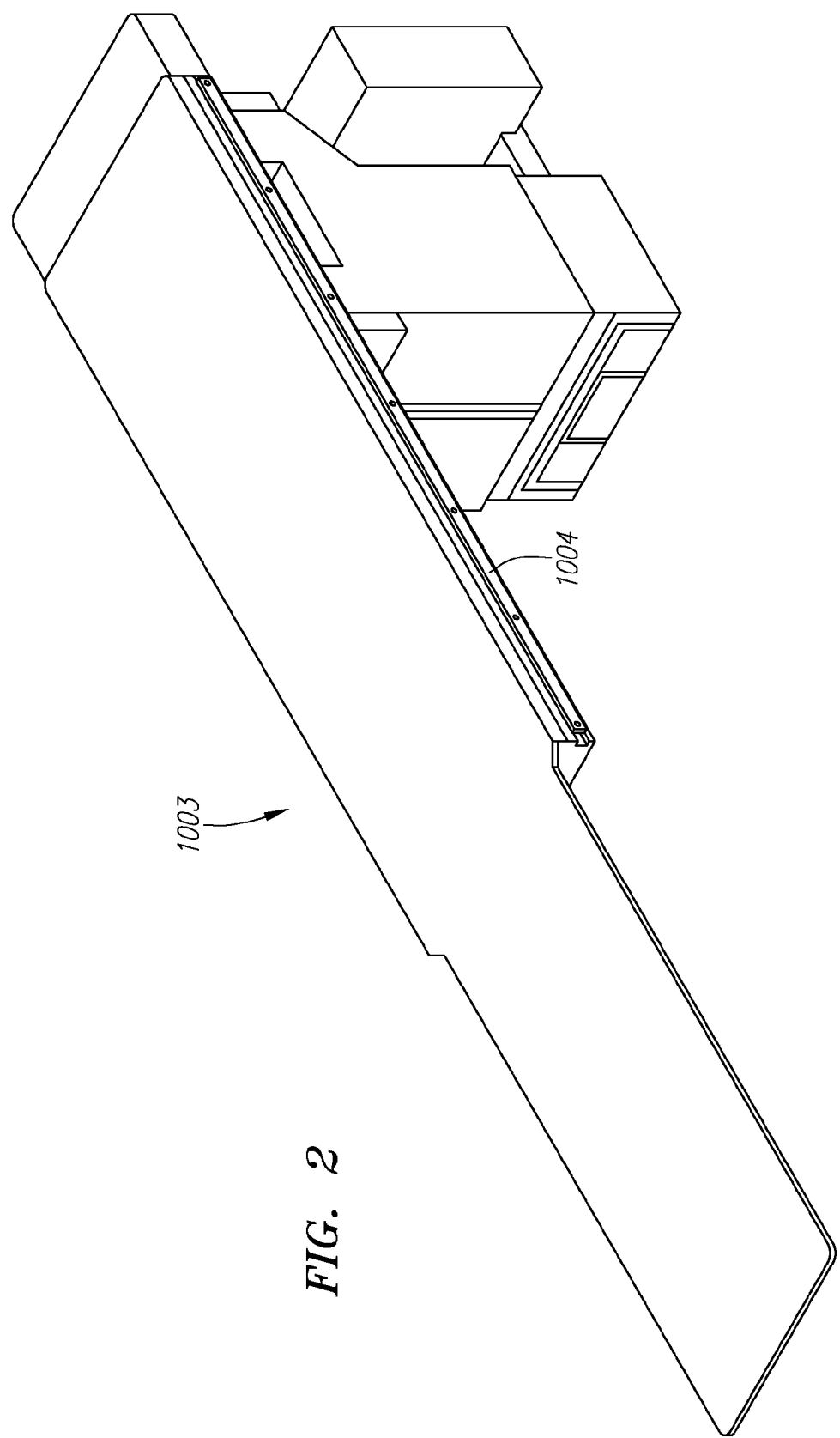
FIGS. 2-3 illustrate exemplary embodiments of operating tables.
Figure 3:
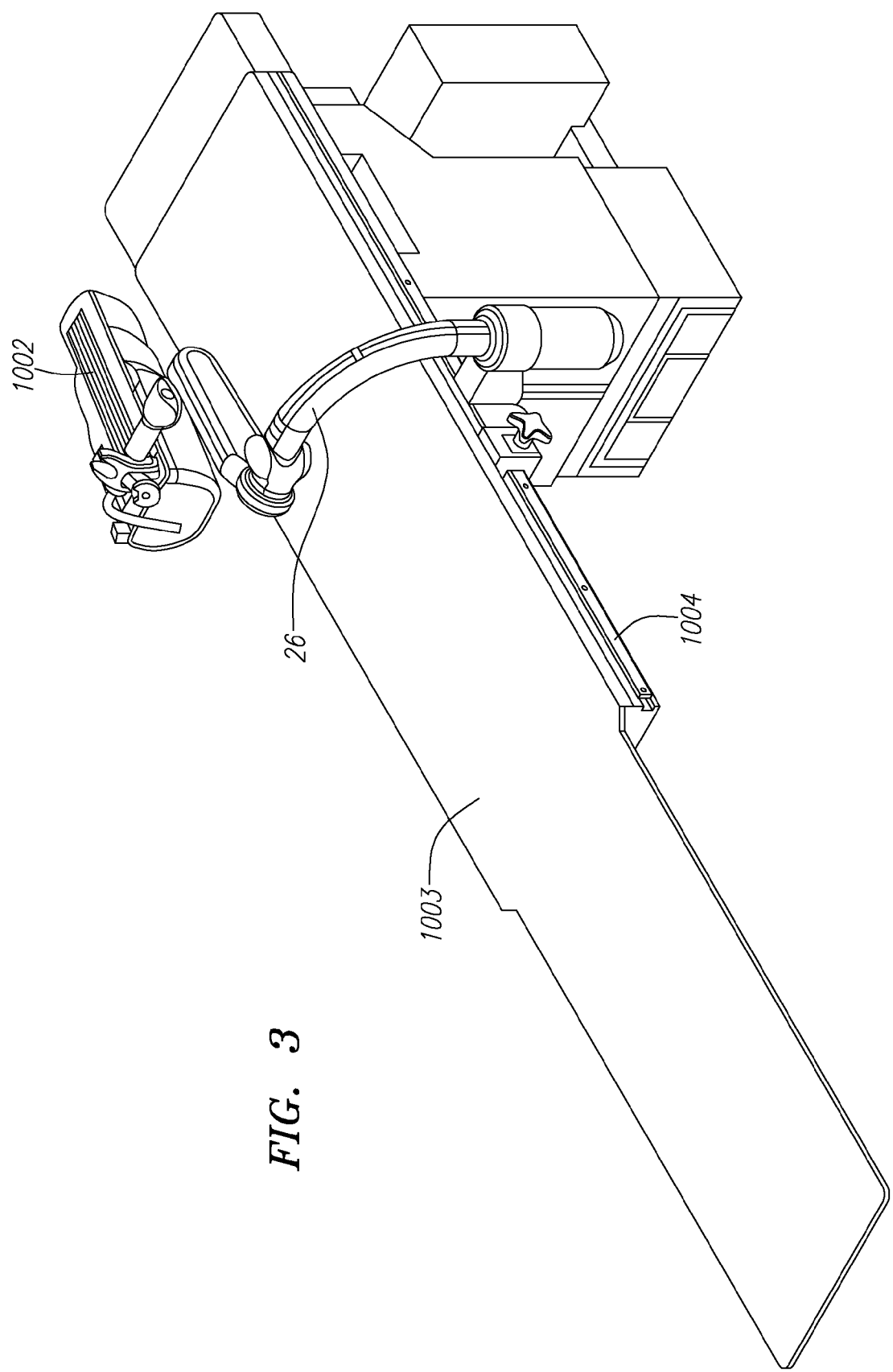
Figure 4:
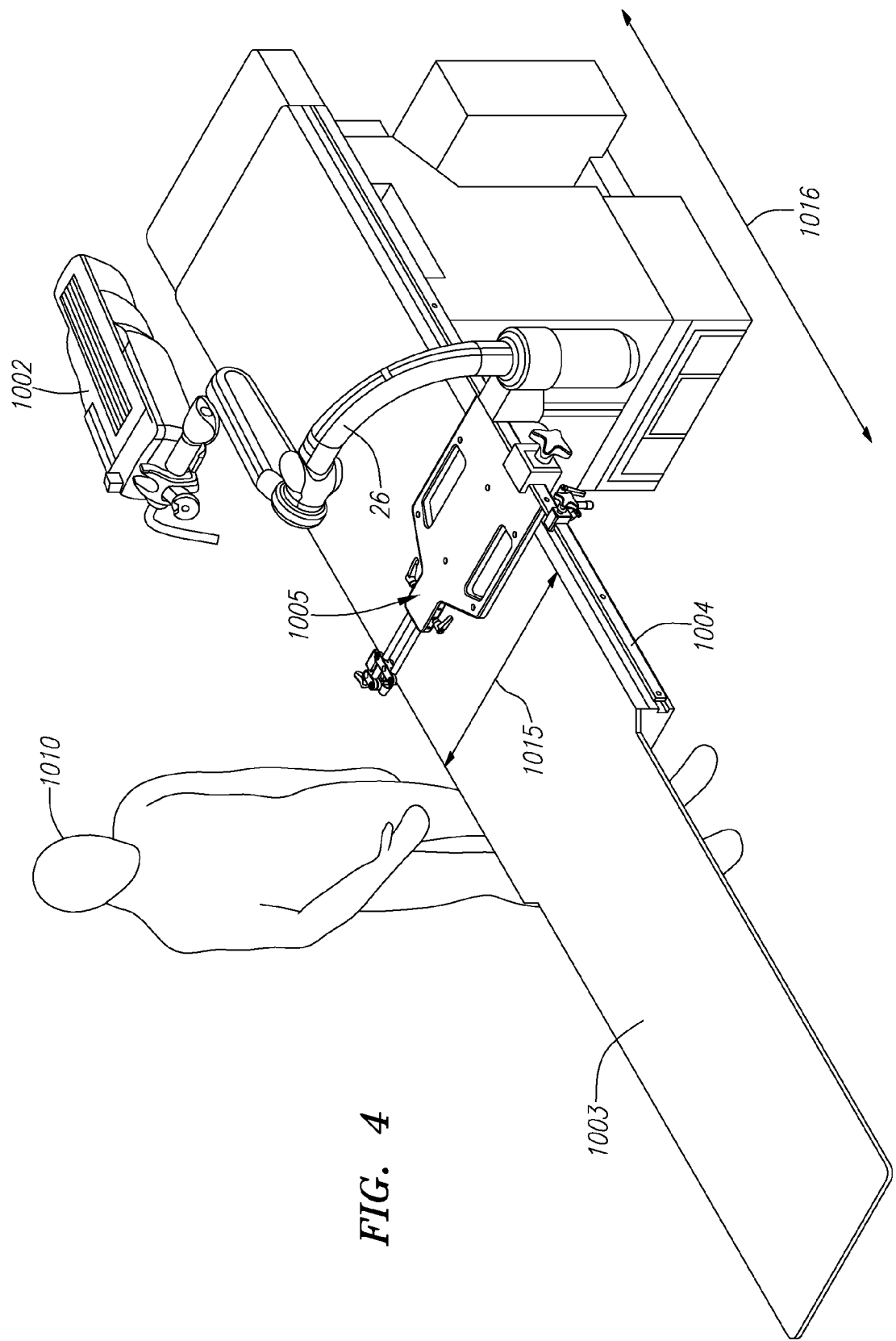
FIGS. 4-9 illustrate embodiments of a support arm adapter base plate assembly for attaching a support assembly to a operating table.
Figure 5:
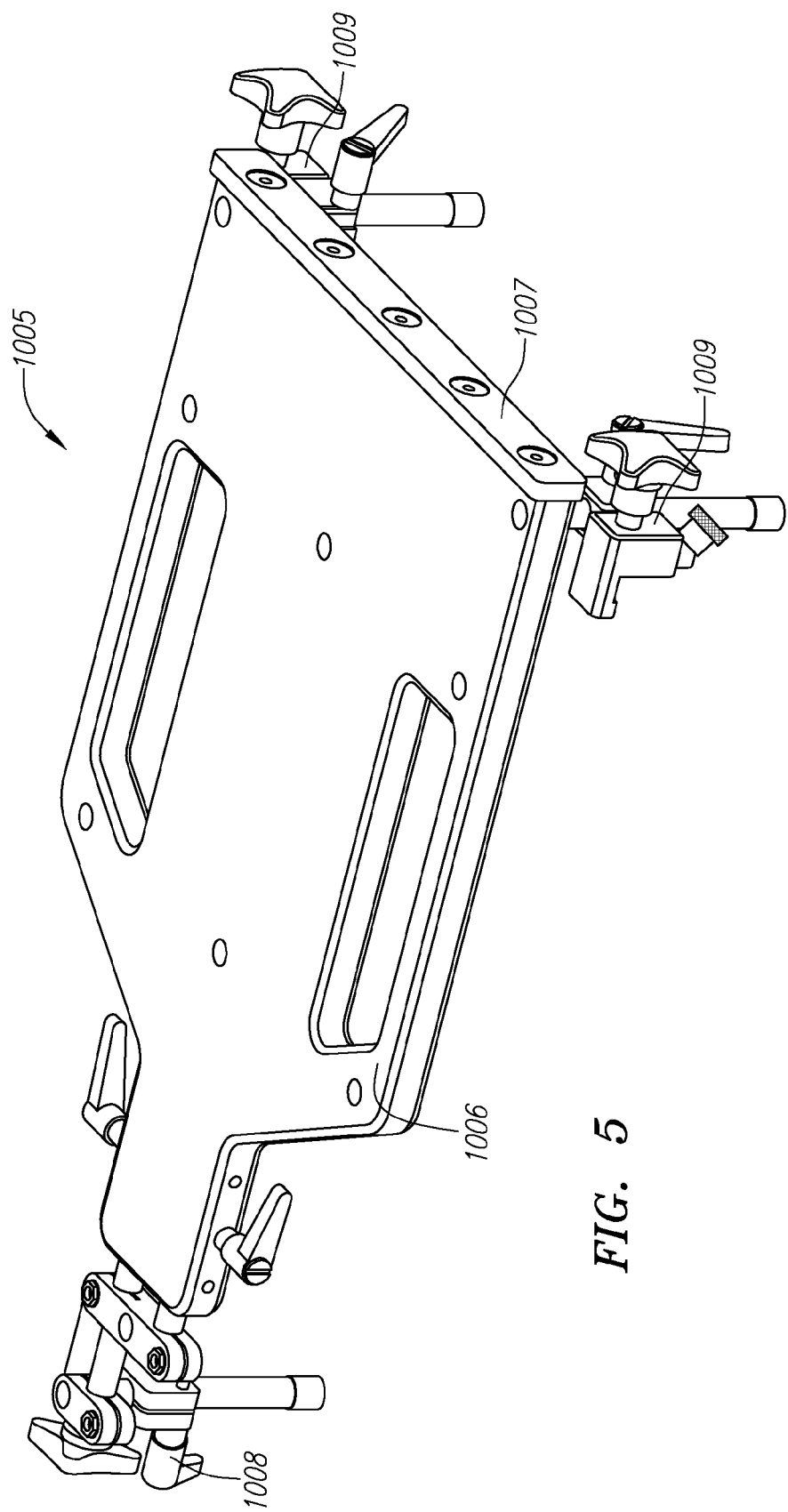
Figure 6:
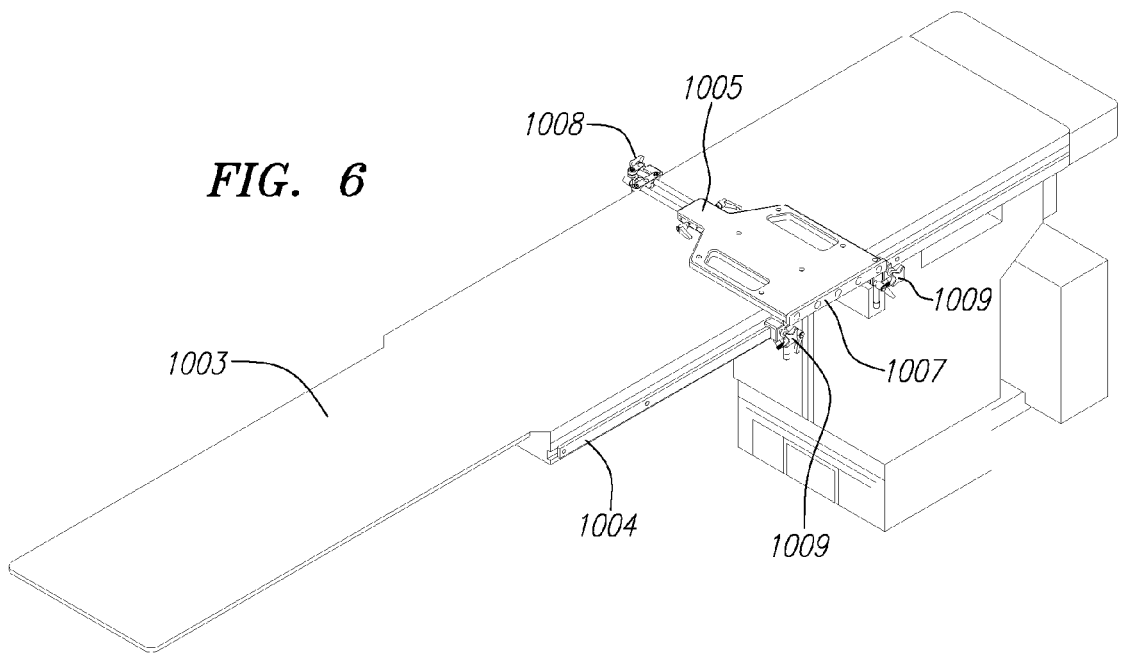
Figure 7:
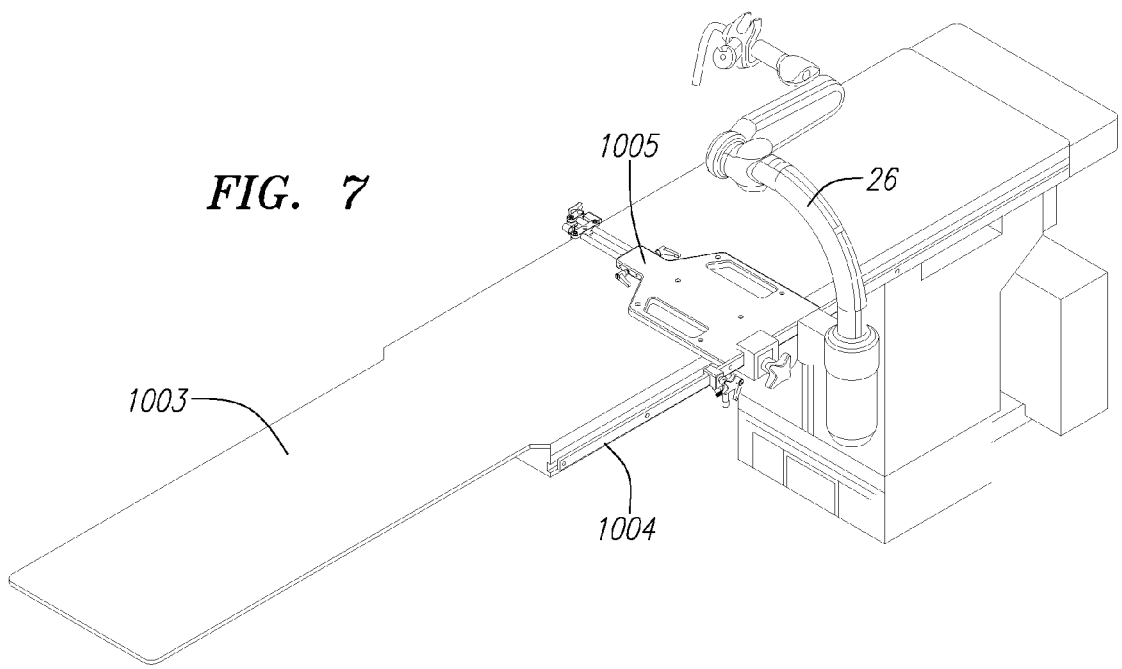
Figure 8:
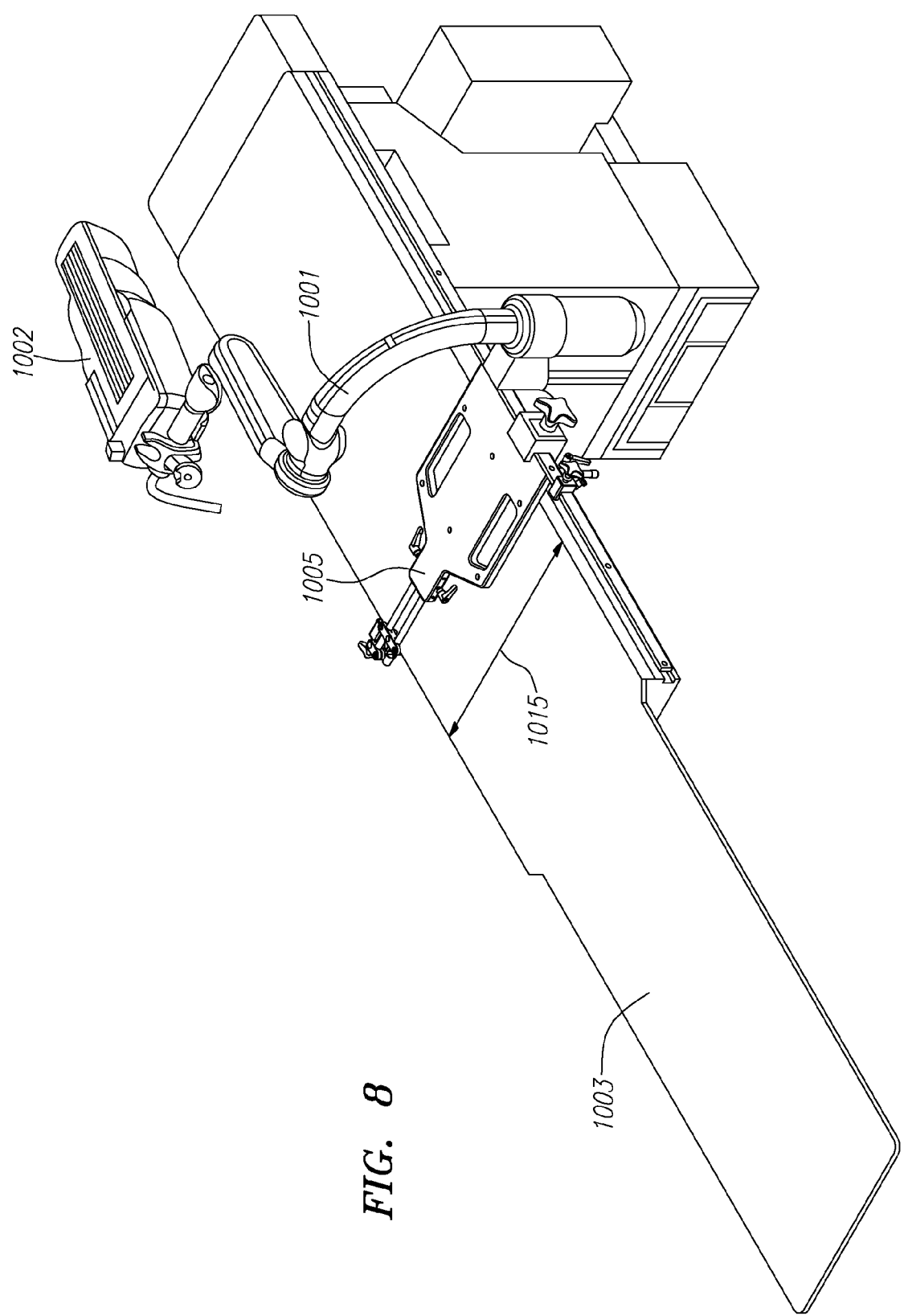

Referring now to FIGS. 2-3, an exemplary operating table (1003) is illustrated. The designs and specifications of operating tables vary widely from manufacturer to manufacturer. Operating tables (1003) not only differ between manufacturers but also between different models from the same manufacturer. Thus it is desirable to have a uniform mounting platform upon which the support assembly (26) for the above described robotic instrument system (32) may be deployed, regardless of the brand of a operating table. Furthermore, it is desirable to have a universal mounting platform that is easily adjustable and adaptable to as many different tablerails as possible. As illustrated in FIG. 1C, one embodiment of a setup joint (26) is designed to mount directly to a tablerail (1004). As a result, variations in tablerail dimensions including cross section on rails, vertical elevation, and width result in a complicated, adjustable design for the setup joint tablerail clamp (89). In some instances, the tablerails (1004) of some operating tables have shown to be weak, thus providing inadequate stiffness to support the weight of the support assembly (26) and robotic instrument assembly (1002). This may result in an unstable support assembly.

Referring to FIGS. 4-9, embodiments of a support arm adapter base plate assembly (1005) for attaching a support assembly to a operating table (1003). Adapter plate assembly (1005) mounts directly to the operating table (1003). In turn, the support assembly (26) is mounted to the adapter plate assembly (1005). In one embodiment, the adapter plate assembly (1005) comprises a large, flat main plate (1006) which lays on top of a operating table (1003). In one implementation, the assembly (1005) is designed with various adjustments to allow it to be mounted to different types of operating table. On a first edge of the adapter plate assembly (1005) is an adapter plate rail (1007) that is the same or similar to the construction of a traditional operating table rail (1004). By placing this rail (1007) on the adapter plate (1005) itself, a user may be assured that the rail on which a support assembly (26) will be mounted will have having consistent dimensions. The plate rail (1007) may be attached to the main plate (1006), such as by bolting, welding, or other suitable method, or it may be integral to the main plate (1006). Furthermore, the large, flat surface of the main plate (1006) of this embodiment provides stability by distributing the weight of the support assembly (26) and robotic instrument assembly (1002) over a relatively large area of the table, whereas a support assembly (26) mounted directly to the operating table rail (1004) causes its entire load to be placed on a limited portion of the table rail (1004). In order to mount this embodiment of an adapter plate assembly (1005), a clamp assembly (1008) and a clamp assembly (1009) are located on opposing sides of the adapter plate assembly (1005) and are configured to clamp the assembly to the operating table (1003). The clamp assembly (1008) is attached to one side of the main plate (1006) such that the first clamp assembly (1008) is located on one side of the operating table when the adapter plate assembly (1005) is installed; and the clamp assembly (1009) is attached to the opposing side of the main plate (1006) such that the clamp assembly (1009) is located on the other side of the operating table (1003) when the adapter plate assembly (1005) is installed. In this embodiment, a single clamp assembly (1008) is used on the surgeon (1010) side of the assembly while two assemblies (1009) are used on the opposite side. It is contemplated that in alternative embodiment, varying numbers of clamp assemblies (1008 and 1009) may be employed on each side of the plate assembly (1005). In this example, a single clamp assembly (1008) is used on the surgeon side of the table (1003) to minimize the amount of tableside space taken up by the adapter plate assembly (1005).

Figure 9:
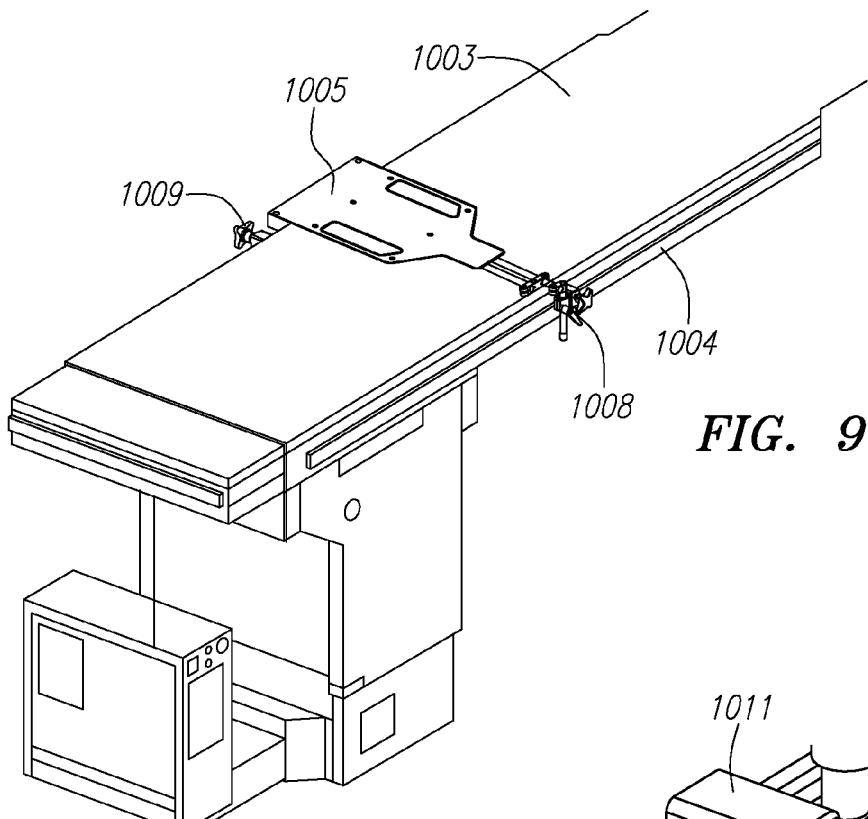

To mount the adapter plate assembly (1005), the clamp assembly (1008) on the surgeon side (1010) of the table may be removed or extended out of the way and the adapter plate assembly (1005) is placed on the top surface of the operating table (1003). The clamp assembly (1008) is repositioned on the adapter plate assembly (1005) and the clamp assemblies (1008 and 1009) on both the surgeon side 1010 and the opposing side of the table are tightened onto the operating table rails (1004). The support assembly (26) may then be mounted to the adapter plate rail (1007) and placed over the entire adapter plate assembly (1005). FIG. 9 illustrates a operating table (1003) with adapter plate assembly (1005) installed from the surgeon (1010) side of the table (1003).

Figure 9A:
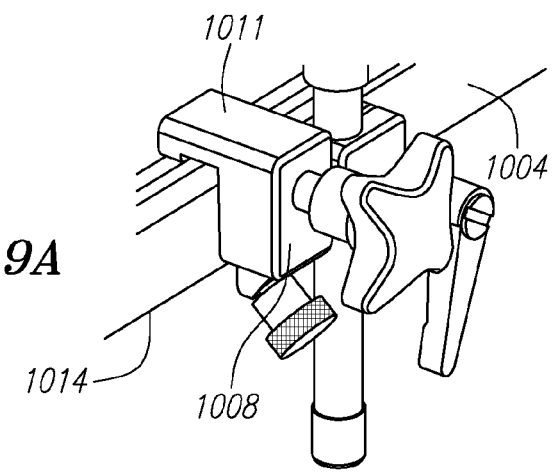
Figure 10:
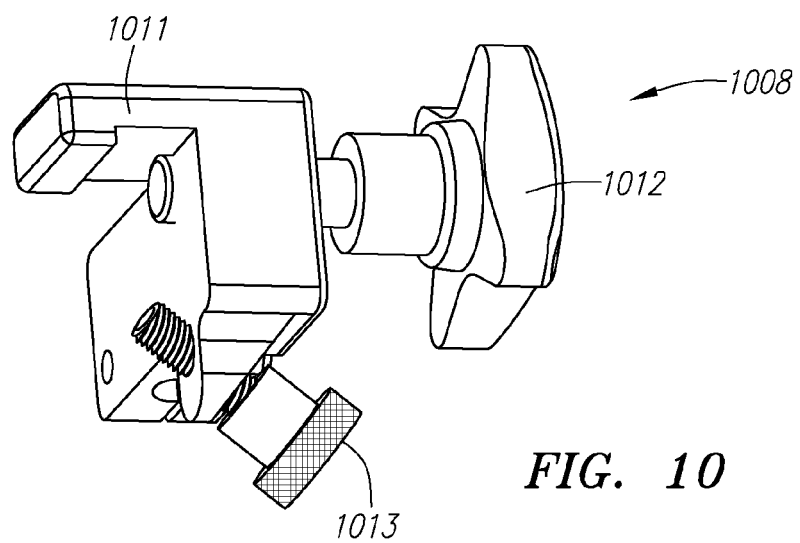
Figure 20:
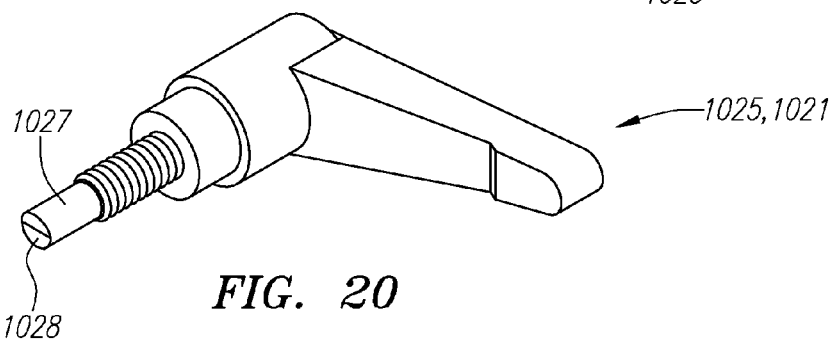
FIGS. 20-21 illustrate different views of one embodiment of an adjustment knob.

Referring to FIGS. 9A and 10, one embodiment of a clamp assembly (1008/1009) is illustrated. FIG. 9A illustrates a first perspective view of a clamp assembly (1008) mounted to a table rail (1004). FIG. 20 illustrates another perspective view of a clamp assembly (1008). In one embodiment, the clamp assemblies (1008/1009) on both sides of the adapter plate assembly (1005) are identical in design. Each clamp assembly (1008/1009) comprises an upside down L-shaped metal clamp (1011) which hooks around the top of the table rail (1004). The clamp assembly (1008) fits on top of the table rail (1004) and a large knob (1012) threaded through clamp (1011) may be adjusted to tighten directly against the table rail (1004), thus pulling the hook of the clamp (1011) against the table rail (1004) and locking the clamp (1011) in place. Another knob (1013) is threaded through the clamp (1011) directly below the large knob (1012) but is threaded through at an upward angle. This angled knob (1013) catches the underside (1014) of the table rail (1004). The knob (1013) serves as a secondary locking mechanism to the main knob (1012) and also prevents any twisting due to an unexpected large moment about the operating table.

Figure 11:
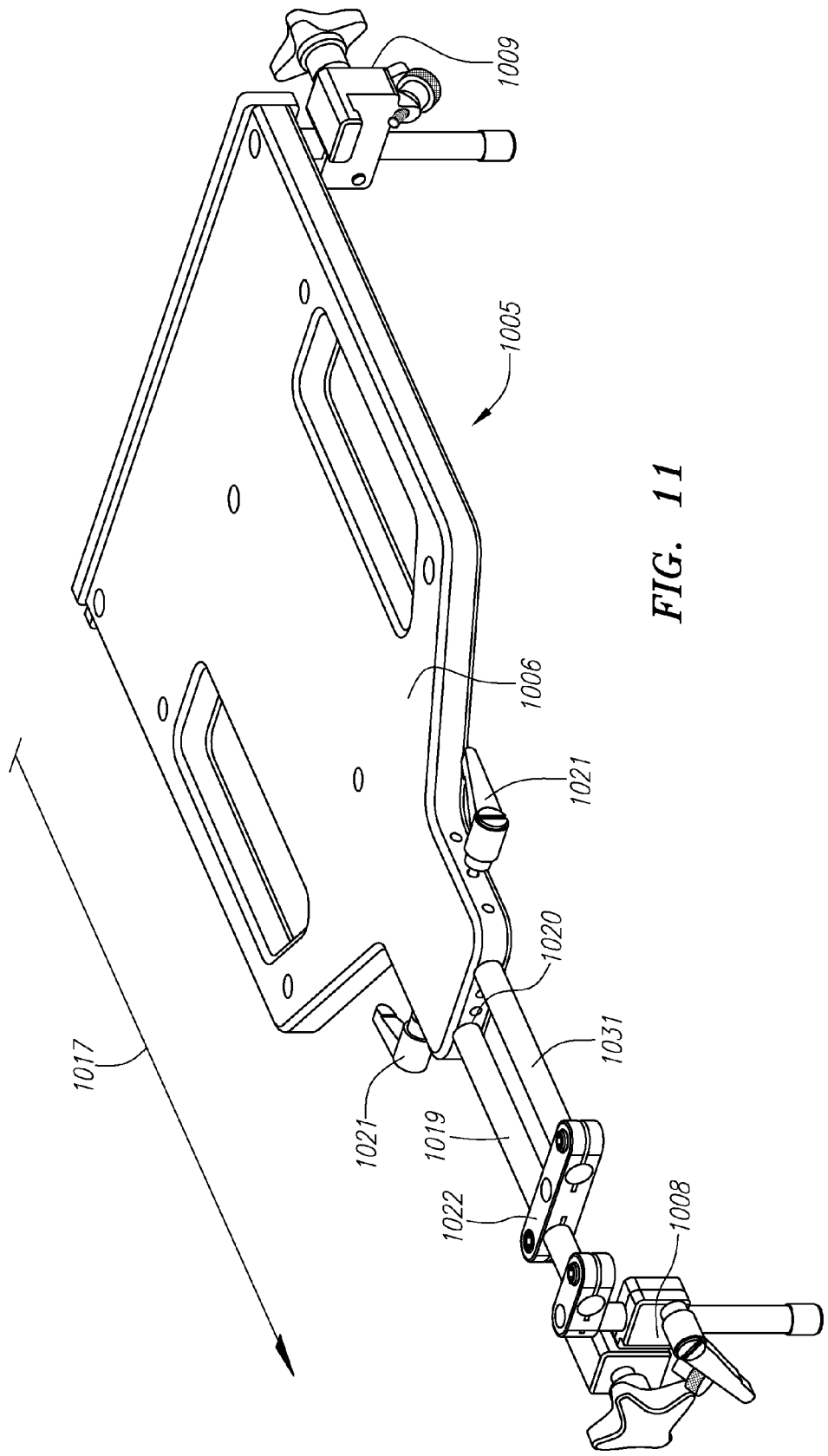
FIG. 11 illustrates a perspective view of one embodiment of an adapter plate assembly.
Figure 12:
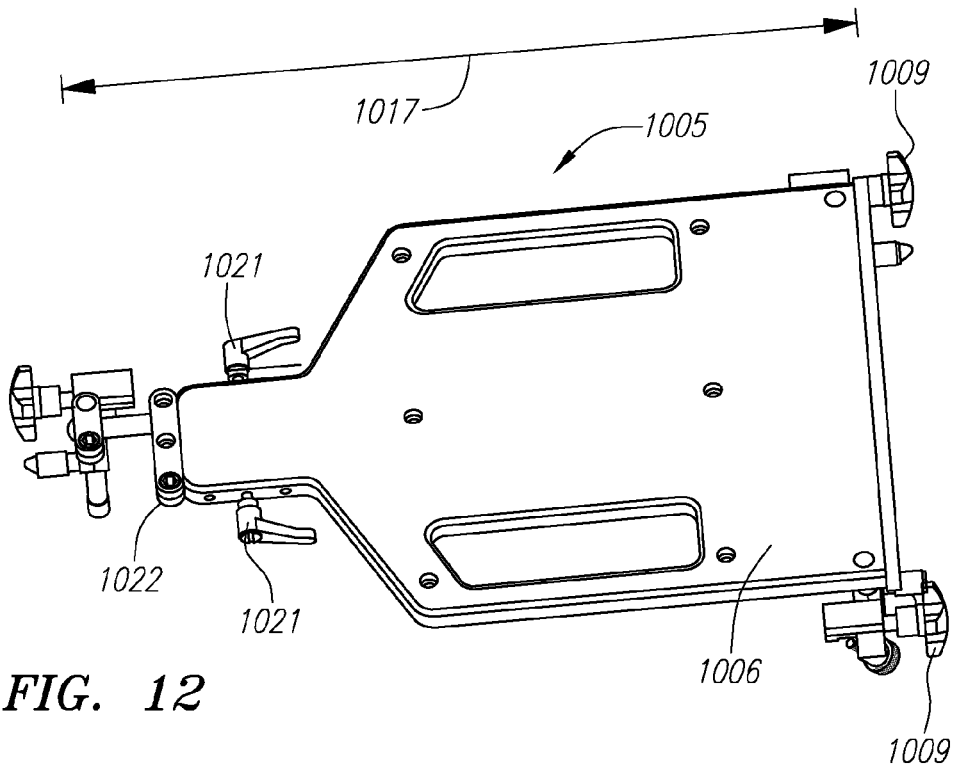
FIG. 12 illustrates the adapter plate assembly of FIG. 11 in a first, retracted configuration.
Figure 13:
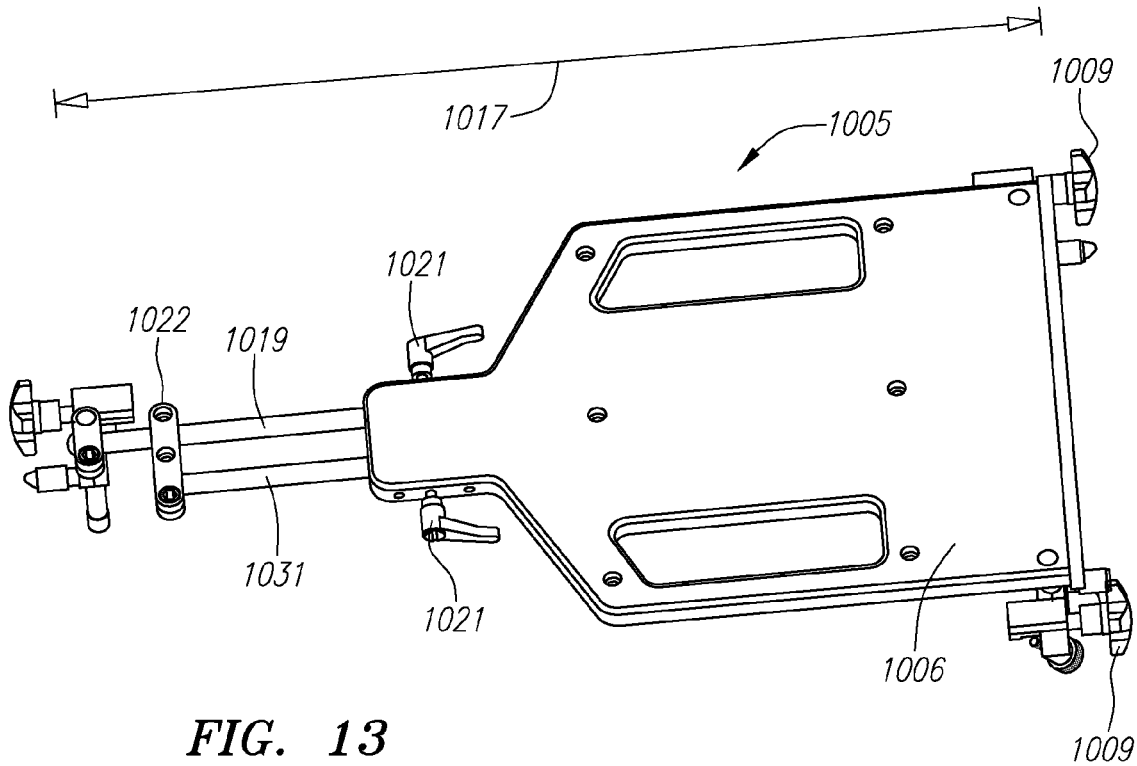
FIG. 13 illustrates the adapter plate assembly of FIG. 11 in a second, extended configuration.

FIGS. 11-13 illustrate a first manner of adjustment of an embodiment of the adapter plate assembly (1005) which allows the plate assembly (1005) to be installed on operating tables (1003) that have different widths. FIGS. 11 and 12 illustrate another perspective view of one embodiment of the adapter plate assembly (1005) in a first, retracted configuration. FIG. 13 illustrates the adapter plate assembly in a second, extended configuration. The first adjustable element of the adapter plate assembly (1005) concerns the width (1017) of the adapter plate assembly (1005). In this embodiment, the plate assembly (1005) is adjustable to fit the width (1015) of the operating table (1003) (see FIG. 8). In order to accomplish this, the surgeon side clamp assembly (1008) is mounted on two adjustable rods (1019/1031) that fit in two holes (1020) that run parallel to the width (1017) of the adapter main plate (1006) on one end, and are coupled to a split clamp (1022) on the other end. The rods (1019/1031) are held in place by two set knobs (1021) threaded into the main plate (1006). By loosening both set knobs (1021), the rods (1019/1031) are able to slide in and out, thereby essentially increasing and decreasing the effective width of the adapter plate (1005). When the desired width is achieved, the set knobs (1021) are tightened and the rods (1019/1031) are locked into place. Two adjustable rods (1019 and 1031) are used instead of a single rod to prevent the surgeon side clamp (1008) from rotating about the rod (1019) axis. Having two rods also allows for redundancy so that if one rod (1019 or 1031) breaks or if one knob (1021) fails, the other remains to preserve the functionality of the system. Similarly, the one or more clamp assemblies (1009) may also be adjustable to adjust the width of the plate assembly (1005).

Figure 14:
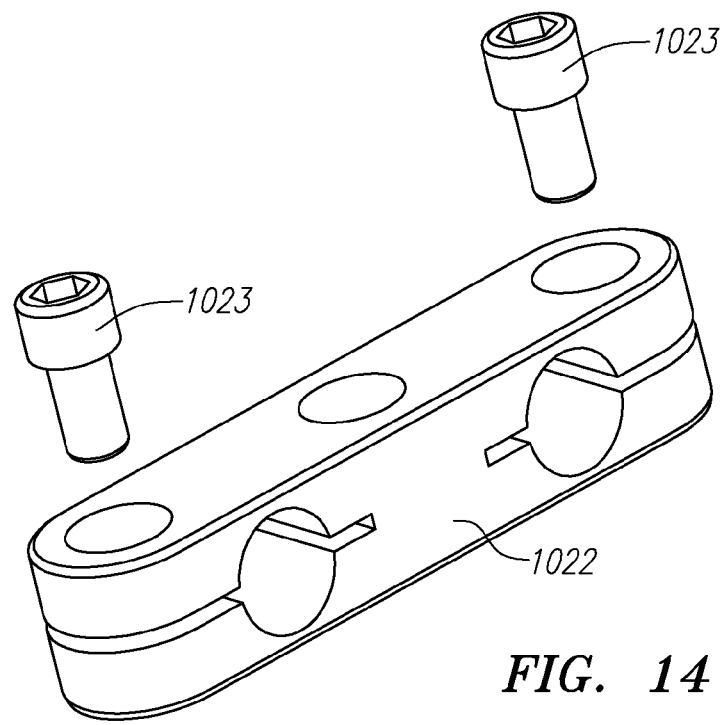
FIGS. 14-15 illustrate one embodiment of a split clamp and associated rods.
Figure 15:
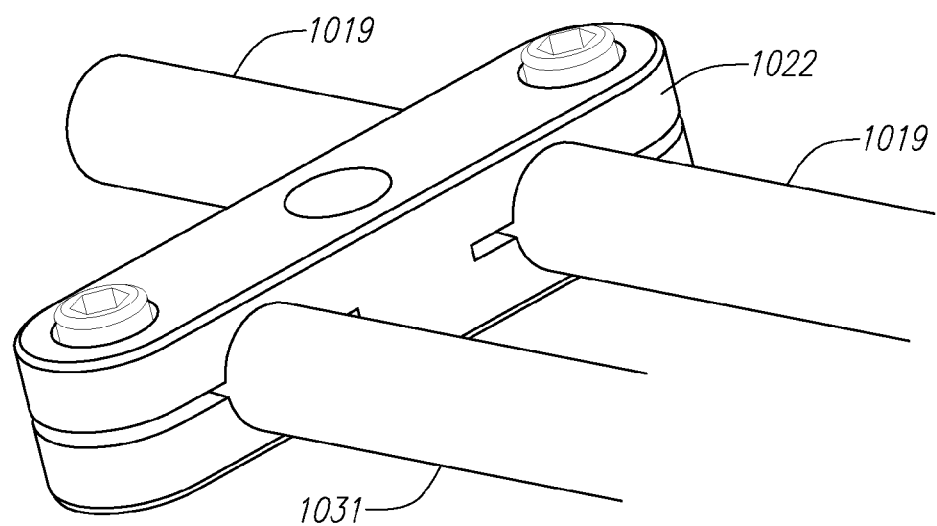

FIGS. 14-15 illustrate the split clamp (1022) and associated rods (1019/1031). The adjustable rods (1019/1031) are held at their distal ends with a split clamp (1022). The split clamp (1022) is tightened with screws (1023) that sandwich and tighten the split clamp (1022) around the rods (1019 and 1031). One of the rods (1019) extends beyond the main split clamp (1022) to the distal end of the assembly where it couples to the clamp assembly (1008). In one embodiment, the adjustable rods (1019/1031) are configured such that the adapter plate assembly (1005) may extend its width (1017) to about 36 inches, or more. In a case where a table may be wider than 36 inches, the rods (1019/1031) may be replaced with longer length rods.

FIG. 16 illustrates an enlarged perspective view of the portion of one embodiment of a plate assembly (1005) near the surgeon side. FIGS. 17-18 illustrate an enlarged perspective view of the clamp assembly (1008) of one embodiment. In this implementation, the clamp assemblies (1008/1009) for a single plate assembly are identical. A clamp assembly is now described. Each clamp assembly (1008/1009) also allows for a vertical adjustment. Because the distance between the top surface of the table (1003) and the table rail (1004) can vary as much as 3-4 inches from table-to-table, a height adjustment on the clamp assembly (1005) is needed in order to be able to mount the adapter plate clamps (1008/1009) to different types of tables. The vertical adjustment is achieved by providing the clamp component (1011) with a split clamp (1023) that can slide up and down on a vertical rod (1024). The split clamp (1023) in its relaxed state has an inner diameter that is larger than the outer diameter of the vertical rod (1024). A threaded set knob (1025) passes through a through-hole in one side of the clamp (1023) and threads into the other side so that when the knob is tightened, the split clamp (1023) closes, decreasing its inner diameter and locking it onto the vertical rod (1024). The maximum vertical adjustment is obtained by sliding the clamp assembly (1008/1009) to the bottom of the vertical rod (1024). If it becomes necessary to extend the vertical maximum for extremely thick tablerails, the vertical rods (1024) could be swapped out for longer rods. Although currently the vertical rods (1024) are pressed and pinned into the clamp component (1011), an alternative embodiment may include swappable rods. In another embodiment, the interface between the rod (1024) and the small split clamp (1032) may be threaded together with a locking nut to lock the rod in place.

Figure 19:
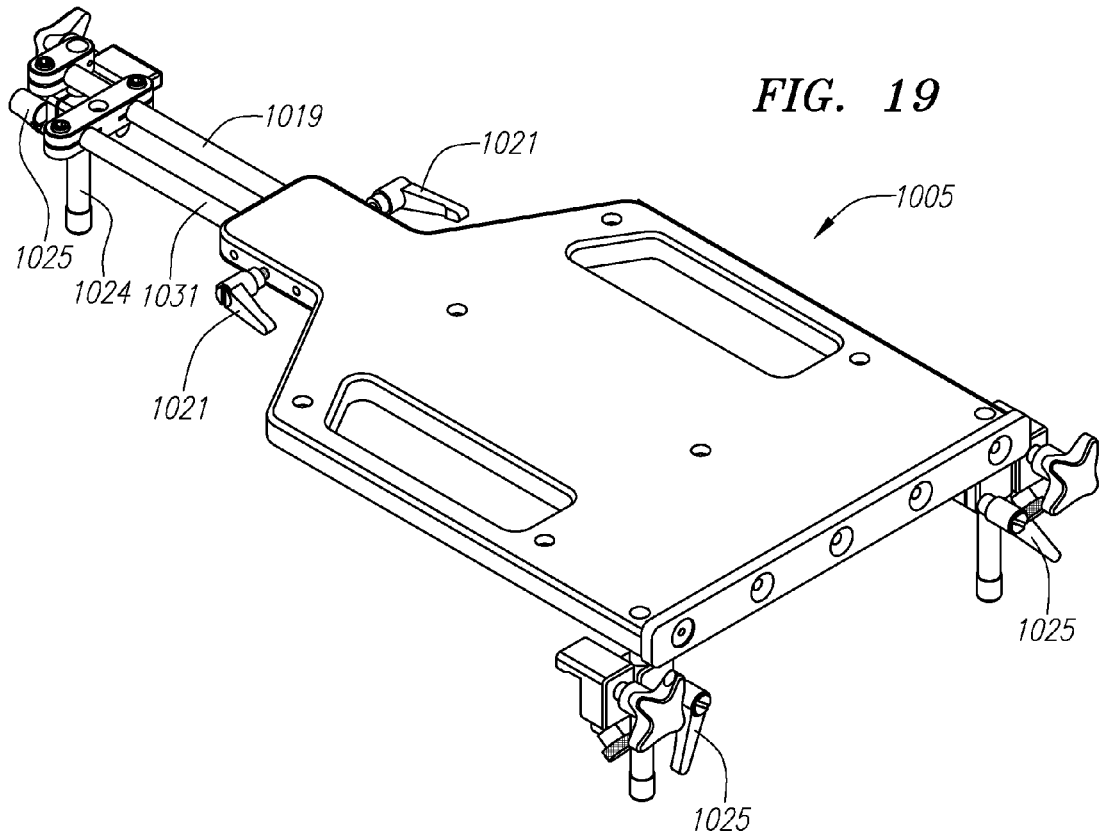
FIG. 19 illustrates another perspective view of one embodiment of the adapter plate assembly.
Figure 21:
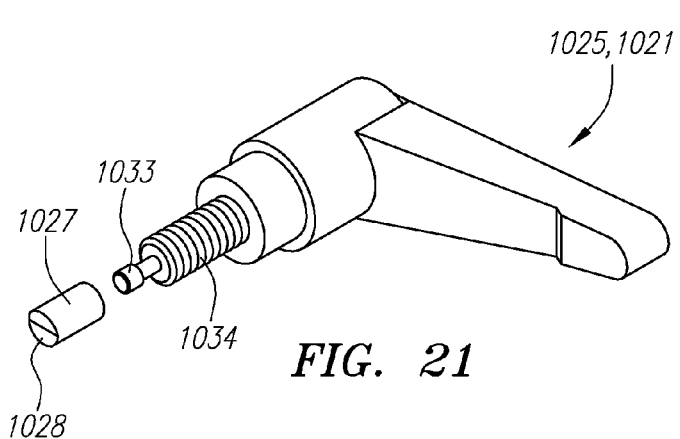

FIG. 19 illustrates another perspective view of one embodiment of the plate assembly (1005). FIGS. 20-21 illustrate different views of one embodiment of the adjustment knob (1021/1025). The set knobs (1021) are used for adjustment of the clamp assemblies (1008 and 1009) and the set knobs (1025) are used for adjustment of the adapter plate width adjustment rods (1019/1031). The set knobs (1021/1025) may be a ratchet type knob for safety wherein the knob does not engage its threads by simply spinning the knob. In order to engage the threads, the knob has to be forced down into the threads along its spinning axis while spinning the knob. A locking element (1027) is threaded on the distal end of the adjustment knob (1021 and 1025). The locking element (1027) comprises a groove (1028) that matches the adjustable rods (1019/1031) and vertical rod (1024) such that the groove can press up against the respective rod and lock it into place. The locking element (1027) is threaded onto the knob (1021/1025) to capture it in the assembly so when the rod (1019/1031/1024) is removed from the assembly the locking element (1027) does not fall out. In one embodiment, the threads on the distal portion (1033) of the adjustment knob are reversed from the threads on the proximal end (1034), i.e. left handed threads to prevent the locking element (1027) from loosening when the adjustment knob (1021/1025) is tightened into place to lock the adjustment rod (1019/1031/1024).

Figure 18A:
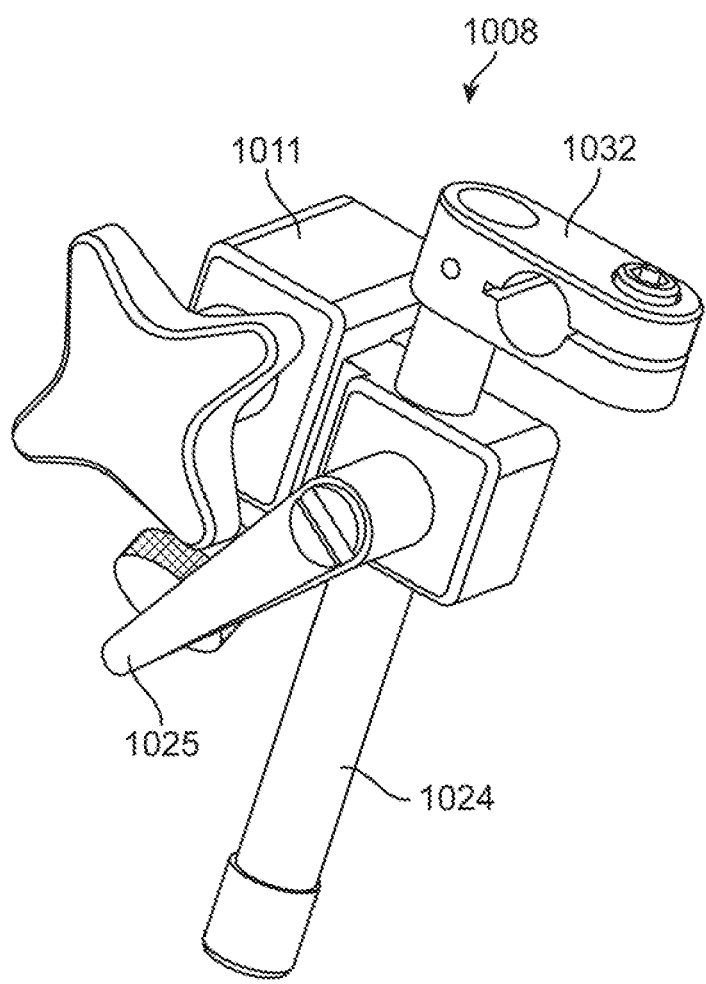
FIG. 18a illustrates another embodiment of a clamp assembly.

FIG. 18a illustrates an enlarged perspective view of another embodiment of a clamp assembly 1008 which utilizes the locking set knob 1025 shown in FIGS. 20-21, as just described. The locking element (1027) comprises a groove (1028) that matches the vertical rod (1024) such that the groove can press up against the vertical rod and lock it into place.

Figure 22:
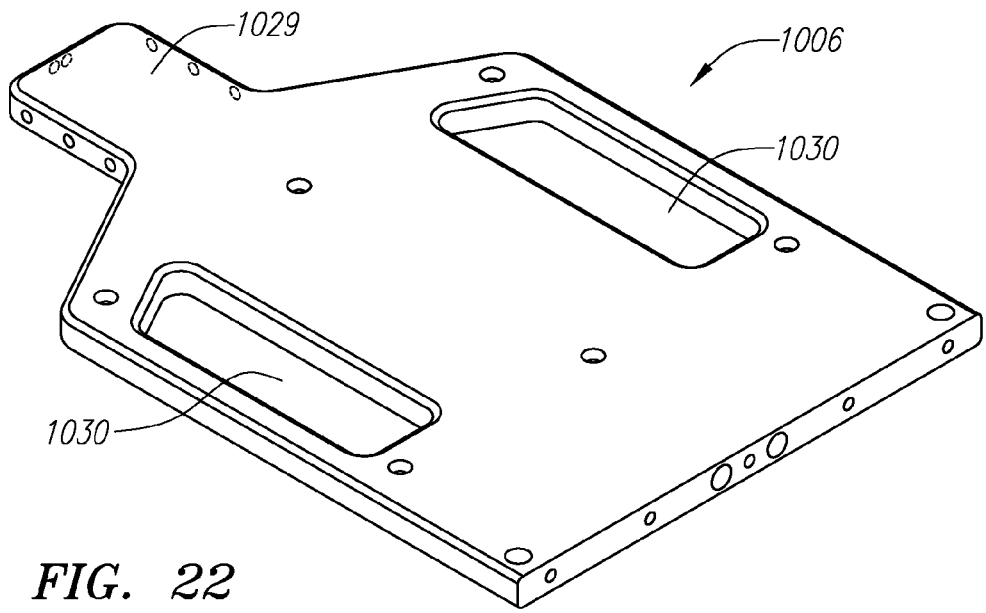
FIGS. 22-23 illustrate different views of one embodiment of the main plate of the adapter plate assembly.
Figure 23:
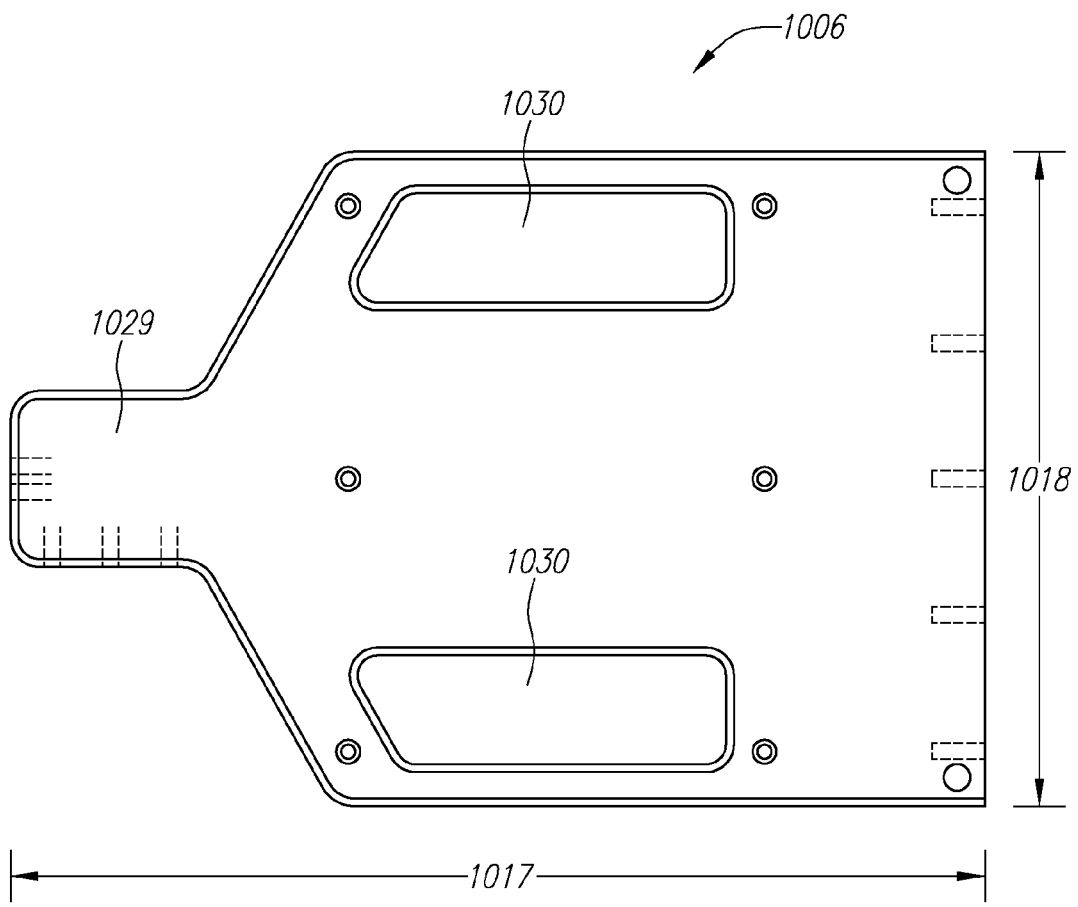

FIGS. 22-23 illustrate different views of one embodiment of the main plate (1006) of the adapter assembly (1005). From a top view, the adapter main plate (1006) is shaped like a rectangle that tapers off to create a neck like portion (1029). The main plate (1006) is shaped so that its width dimension in the neck like portion (1029) is smaller on the surgeon (1010) side of the table and has a much wider width (1018) on the opposite side of the table. The wide length (1018) on the opposite side of the table is intended to increase stability and safety. First, the wide edge (1018) allows for two clamp assemblies (1009) that can be spaced further apart. Second, increasing the overall size of the plate gives the plate (1006) some size and weight to safely hold the support arm assembly (26) and instrument driver (1002) in place even if the clamp assemblies (1008/1009) are mistakenly loosened or insufficiently tightened. The smaller width neck (1029) of the main plate (1006) in this example is intended to reduce the amount of table rail (1004) space used on the surgeon side of the table (1003). In some instances, a operating table (1003) may have several pendants mounted to its table rail (1004) on the surgeon side (1010) for flouroscopy, display screens, ablation tools, etc. Thus the necking (1029) in one embodiment of a plate reduces the need of the table rail (1004) space to approximately 3 inches. In alternative embodiments, this necking may be reduced or eliminated such that the surgeon side of the plate may be resized to wider dimensions as desired. Additionally, one of the adjustable rods (1019) is extended to hold the clamp assembly (1008). The rod (1019) is extended to be able to achieve the minimal three inch tablerail (1004) space taken by the single clamp assembly (1008). A smaller split clamp (1032) holds the distal end of the fixed rod (1019) and functions identically to the split clamp (1022). For one implementation, the thickness of the main plate (1006) is chosen to be ¾" inch. Because the plate is installed underneath a patient's feet, it is important that the thickness of the plate does not elevate the feet significantly. With more clinical data, the thickness of the main plate (1006) can be increased. When the adjustable rods (1019/1031) are pulled out to extend the width of the plate assembly (1005), the extended portion (1035) (see FIG. 24) of the assembly does not include the thickness of the main plate (1006). Should a patient lying on the surgical table have one foot elevated by the main plate a greater amount than the other foot, a block can be placed over the rods to correct for this height discrepancy. The main plate (1006) also includes a pair of cut-outs (1030) which can be used as handles for handling the plate assembly (1005) and also to reduce the overall weight of the main plate (1006).

Figure 24:
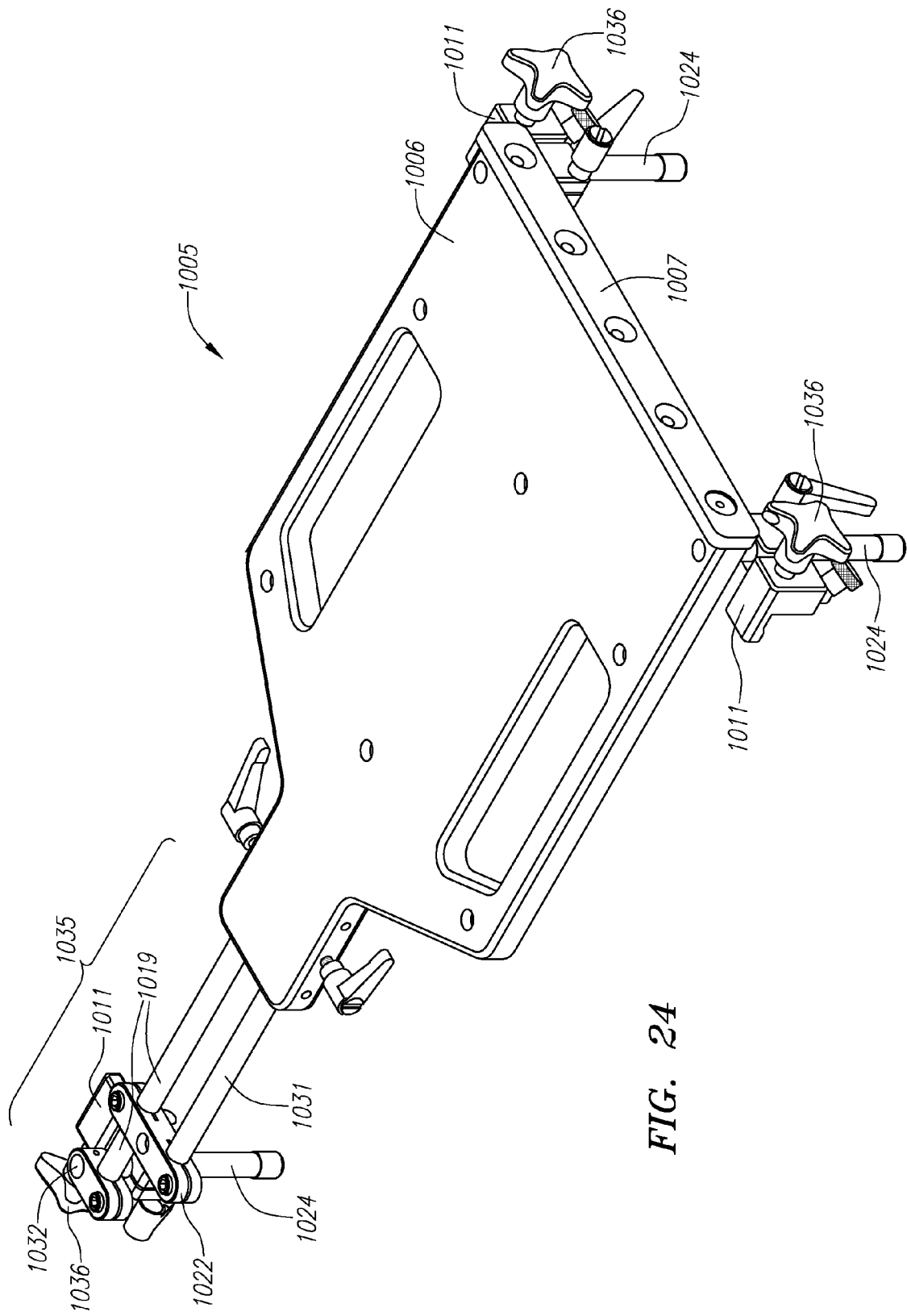
FIG. 24 illustrates yet another view of the adapter plate assembly of one embodiment.

FIG. 24 illustrates yet another view of one embodiment of the adapter plate assembly (1005). In one implementation, the main plate (1006) is aluminum and the adapter plate rail (1007) is steel. In alternative embodiments, other types of materials, metallic or non-metallic, may be used to construct the various elements of the adapter plate assembly (1005). The adjustment rods (1019/1031/1024) (both for width and vertical adjustments) of this embodiment may be constructed of steel. The split clamps (1022/1032) holding the rod (1024) and the adjustable rods (1019/1031) may also fabricated from steel in this embodiment. In other embodiments non-metallic materials such as carbon fibers may be used instead of aluminum and steel. In alternative embodiments, an assembly with a minimal amount of metal may be desirable to reduce interference with any imaging modalities that may be used during a surgical procedure.

Figure 25:
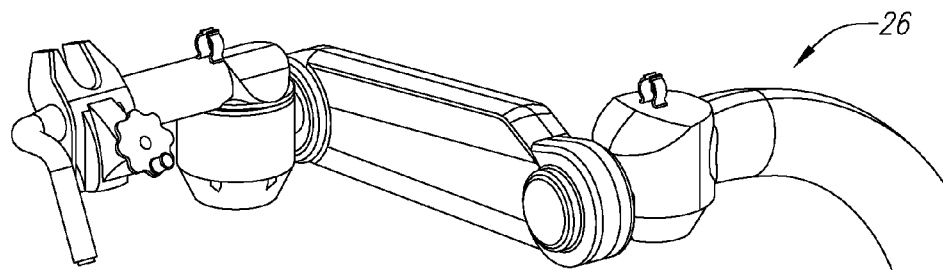
FIG. 25 illustrates one embodiment of a support assembly.
Figure 26:
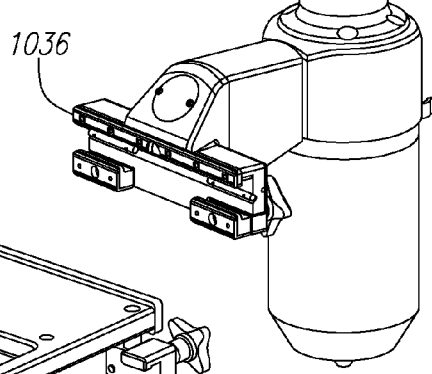
FIG. 26 illustrates one embodiment of an adapter plate assembly oriented to receive the support assembly of FIG. 25.
Figure 28:
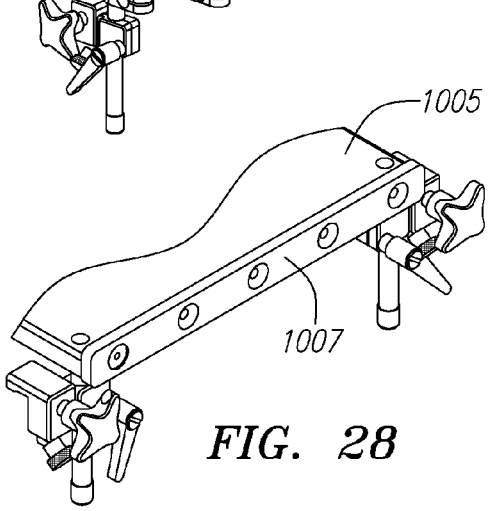
FIG. 28 illustrates an enlarged view of the adapter plate rail for the adapter plate assembly of FIG. 26.
Figure 27:
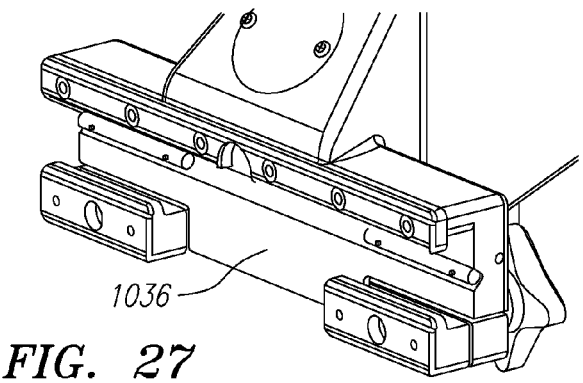
FIG. 27 illustrates an enlarged view of the support assembly interface for the support assembly of FIG. 25.

FIG. 25 illustrates the support assembly (26) of one embodiment. FIG. 26 illustrates one embodiment of an adapter plate assembly (1005) oriented to receive the support assembly (26) of FIG. 25. FIG. 27 illustrates an enlarged view of the support assembly interface surface (1036) for the support assembly (26) of FIG. 35. FIG. 28 illustrates a close up view of the adapter plate rail (1007) for the adapter plate assembly (1005) of FIG. 26. In order to prevent a user from accidentally installing the setup joint (26) directly onto the operating table rail (1004) instead of first installing the adapter plate assembly (1005) and then installing onto the adapter plate rail (1007), the interface between the adapter plate rail (1007) and the support assembly interface (1036) may be specifically keyed. For example, the support assembly interface (1036) can be angled or keyed to match a mirror image shaped surface on the adapter plate rail 1007 so that the setup joint (26) can only be mounted to the adapter plate assembly (1005). Another advantage of this adapter plate platform apparatus is the ability to be able to mount a support assembly (26) anywhere on the operating table, whether it be surgeon side, far side, center of table, etc.

Another embodiment for this adapter plate assembly (1005) is designed to hold multiple support assemblies (26) and multiple instrument drivers (16). By altering the main plate (1006), another rail (1007) may be added to the other side of the table. Furthermore, an additional rail could be added to mount a support assembly (26) that extends from between the patients legs, etc. If desired, a secondary rail can be added on the same side of the adapter plate assembly (1005) that extends further from original rail (1007) such that a pair of support assemblies (26) may be mounted on the same side of the table; or the rail (1007) can be lengthened such that it can accommodate two or more support assemblies (26). Furthermore, the adapter plate assembly (1005) may be configured such that the main plate (1006) is place underneath the operating table (1003), instead of on top of the operating table (1003).

While multiple embodiments and variations of the many aspects of the invention have been disclosed and described herein, such disclosure is provided for purposes of illustration only. Many combinations and permutations of the disclosed system are useful in minimally invasive surgery, and the system is configured to be flexible, and it should be understood that the invention generally, as well as the specific embodiments described herein, are not limited to the particular forms or methods disclosed, but also cover all modifications, equivalents and alternatives falling within the scope of the appended claims.

What is claimed is:

1. An adapter plate assembly for mounting a support assembly used for suspending an instrument driver above an operating table, comprising:
    a substantially flat main plate having top and bottom surfaces, first and second ends, and two sides;
    a first clamp assembly coupled to the first end of the main plate and having a first clamp configured for removable attachment to the operating table, the first clamp assembly being extendable from the main plate first end so as to allow for adjusting a width of the adapter plate assembly to accommodate a width of the operating table, the first clamp assembly having a first split clamp which releasably couples to a first vertical adjustment rod, wherein the first split clamp may be released to allow the position of the first clamp assembly to be adjusted vertically along the first adjustment rod to adjust a respective height of the first clamp relative to the top surface of the main plate, and wherein the first split clamp can be tightened to secure the first split clamp to the first adjustment rod;
    a second clamp assembly coupled to the second end of the main plate and having a second clamp configured for removable attachment to the operating table, the second clamp assembly having a second split clamp which releasably couples to a second vertical adjustment rod, wherein the second split clamp may be released to allow the position of the second clamp assembly to be adjusted vertically along the second adjustment rod to adjust a respective height of the second clamp relative to the top surface of the main plate, and wherein the second split clamp can be tightened to secure the second split clamp to the second adjustment rod; and
    an adapter rail coupled to the second end of main plate, the adapter rail configured to detachably couple to a support assembly interface and provide sufficient structural support for suspending the instrument driver above the operating table.

2. The adapter plate assembly of claim 1, wherein the first clamp assembly is mounted on an adjustment rod which is slidably received in the main plate and configured to allow the first clamp to be extended and retracted from the main plate so as to adjust the width of the adapter plate assembly to accommodate the width of the operating table, and further comprising a locking device for securing the adjustment rod in a desired position.

3. The adapter plate assembly of claim 1, wherein the first clamp assembly is mounted on a horizontal adjustment rod which is slidably received in the main plate, the adjustment rod configured to allow the first clamp to be extended and retracted from the main plate so as to adjust the width of the adapter plate assembly to accommodate the width of the operating table, and further comprising a first locking device for securing the horizontal adjustment rod in a desired position, the first split clamp and second split clamp each comprise a threaded set knob which passes through a through-hole in one side of the respective clamp and threads into the other side so that when the thread set knob is tightened, the split clamp closes, decreasing its inner diameter and locking it onto the respective vertical adjustment rod.

4. The adapter plate assembly of claim 1, wherein the first clamp assembly and the second clamp assembly each comprises:
    an L-shaped clamp body configured to engage a table rail of the operating table;
    a first set screw threaded through the clamp body and configured to tighten directly against the table rail; and
    a second set screw threaded through the clamp at an angle to said first set screw and configured to engage the underside of the table rail.

5. The adapter plate assembly of claim 1, wherein the adapter plate assembly is configured to mount to a top side of the operating table.

6. The adapter plate assembly of claim 1, wherein the adapter plate assembly is configure to mount to a bottom side of the operating table.

7. The adapter plate assembly of claim 1, wherein the adapter rail is configured to detachably couple to two or more support assembly interfaces in order to support two or more support assemblies.

8. The adapter plate assembly of claim 1, further comprising a second adapter rail coupled to the second end of the main plate, the second adapter rail configured to detachably couple to a second support assembly interface.

9. An adapter plate assembly for mounting a support assembly for suspending a medical instrument driver above a operating table, comprising:
    a substantially flat main plate having top and bottom surfaces, first and second ends, and first and second sides;
    a first clamp assembly mounted on a horizontal adjustment rod which is slidably received in the first end of the main plate, the horizontal adjustment rod configured to allow the first clamp assembly to be extended and retracted from the main plate so as to adjust a width of the adapter plate assembly to accommodate a width of the operating table, and further comprising a first locking device for securing the horizontal adjustment rod in a desired position, the first clamp assembly having a second locking device which releasably couples to a first vertical adjustment rod which is coupled to the horizontal adjustment rod, the second locking device being releasable to allow the position of the first clamp assembly to be adjusted vertically on the first vertical adjustment rod to adjust the height of the first clamp relative to the top surface of the main plate, and the second locking device being lockable to secure the second locking device onto the adjustment rod;

a second clamp assembly coupled to the second end of the main plate near the first side of the main plate, the second clamp assembly having a split clamp configured for removable attachment to the operating table, the second clamp assembly having a third locking device which releasably couples to a second vertical adjustment rod which is coupled to the main plate, the third locking device being releasable to allow the position of the second clamp assembly to be adjusted vertically on the second vertical adjustment rod to adjust the height of the second clamp relative to the top surface of the main plate, and the third locking device being lockable to secure the third locking device onto the adjustment rod;

a third clamp assembly coupled to the second end of the main plate near the second side of the main plate, the third clamp assembly having a clamp configured for removable attachment to the operating table, the third clamp assembly having a fourth locking device which releasably couples to a third vertical adjustment rod which is coupled to the main plate, the fourth locking device being releasable to allow the position of the third clamp assembly to be adjusted vertically on the third vertical adjustment rod to adjust the height of the third clamp relative to the top surface of the main plate, and the fourth locking device being lockable to secure the fourth locking device onto the adjustment rod; and an adapter rail coupled to the second end of the main plate, the adapter rail configured to detachably couple to a support assembly interface and, provide sufficient structural support for suspending the instrument driver above the operating table.

10. The adapter plate assembly of claim 9, wherein the first locking device comprises:
    a threaded rod which threads into the main plate, the threaded rod having a proximal end and a distal end;
    a locking element disposed on the distal end of the threaded rod, the locking element having a groove that engages the horizontal adjustment rod; and
    a ratcheting knob disposed on the proximal end of the threaded rod, the ratcheting knob configured such that the knob must be forced down toward the distal end to engage and rotate the threaded rod.

11. The adapter plate assembly of claim 9, wherein the first, second, third and fourth locking devices each comprise:
    a threaded rod having a proximal end and a distal end;
    a locking element disposed on the distal end of the threaded rod, the locking element having a groove that engages its respective vertical or horizontal adjustment rod; and
    a ratcheting knob disposed on the proximal end of the threaded rod, the ratcheting knob configured such that the knob must be forced down toward the distal end to engage the and rotate the threaded rod.

12. The adapter plate assembly of claim 9, wherein the first, second and third clamp assemblies each comprises:
    an L-shaped clamp body configured to engage a rail of the operating table;
    a first set screw threaded through the clamp body and configured to tighten directly against the table rail; and
    a second set screw threaded through the clamp at an angle to the first set screw and configured to engage the underside of the table rail.

13. The adapter plate assembly of claim 9, wherein the adapter rail is configured to detachably couple to two or more support assembly interfaces in order to support two or more support assemblies.

* * * * *

UNITED STATES PATENT AND TRADEMARK OFFICE
CERTIFICATE OF CORRECTION

| | | |
|---|---|---|
| PATENT NO. | : 8,146,874 B2 | Page 1 of 1 |
| APPLICATION NO. | : 12/024883 | |
| DATED | : April 3, 2012 | |
| INVENTOR(S) | : Alan L. Yu | |

It is certified that error appears in the above-identified patent and that said Letters Patent is hereby corrected as shown below:

At Column 12, Claim 11, line 10, "engage the and rotate" should read:

--engage and rotate--

Signed and Sealed this
Twenty-ninth Day of May, 2012

David J. Kappos
*Director of the United States Patent and Trademark Office*